(12) United States Patent
Qiu

(10) Patent No.: US 10,399,946 B2
(45) Date of Patent: Sep. 3, 2019

(54) SOLID FORMS OF AN S-NITROSOGLUTATHIONE REDUCTASE INHIBITOR

(71) Applicant: Alpine Immune Sciences, Inc., Seattle, WA (US)

(72) Inventor: Jian Qiu, Longmont, CO (US)

(73) Assignee: LAUREL THERAPEUTICS LTD., Hangzhou, Zhejiang Province (CN)

( * ) Notice: Subject to any disclaimer, the term of this patent is extended or adjusted under 35 U.S.C. 154(b) by 0 days.

(21) Appl. No.: 15/758,749

(22) PCT Filed: Sep. 9, 2016

(86) PCT No.: PCT/US2016/050974
§ 371 (c)(1),
(2) Date: Mar. 9, 2018

(87) PCT Pub. No.: WO2017/044766
PCT Pub. Date: Mar. 16, 2017

(65) Prior Publication Data
US 2019/0040014 A1 Feb. 7, 2019

Related U.S. Application Data

(60) Provisional application No. 62/216,765, filed on Sep. 10, 2015.

(51) Int. Cl.
C07D 215/20 (2006.01)

(52) U.S. Cl.
CPC ........ C07D 215/20 (2013.01); C07B 2200/13 (2013.01)

(58) Field of Classification Search
None
See application file for complete search history.

(56) References Cited

U.S. PATENT DOCUMENTS

| | | | |
|---|---|---|---|
| 5,480,883 A | 1/1996 | Spada et al. |
| 5,646,153 A | 7/1997 | Spada et al. |
| 5,795,889 A | 8/1998 | Spada et al. |
| 5,882,546 A | 3/1999 | Manero et al. |
| 5,911,913 A | 6/1999 | Manero et al. |
| 6,180,632 B1 | 1/2001 | Myers et al. |
| 7,674,809 B2 | 3/2010 | Makovec et al. |
| 8,546,392 B2 | 10/2013 | Hartmann et al. |
| 8,785,643 B2 | 7/2014 | Sun et al. |
| 8,921,562 B2 | 12/2014 | Sun et al. |
| 9,012,646 B2 | 4/2015 | Sun et al. |
| 9,139,528 B2 | 9/2015 | Sun et al. |
| 9,221,810 B2 | 12/2015 | Sun et al. |
| 9,315,462 B2 | 4/2016 | Sun et al. |
| 9,364,481 B2 | 6/2016 | Sun et al. |
| 9,433,618 B2 | 9/2016 | Sun et al. |
| 9,856,219 B2 | 1/2018 | Sun et al. |
| 2002/0128205 A1 | 9/2002 | Stamler et al. |
| 2002/0151544 A1 | 10/2002 | Hayakawa et al. |
| 2003/0088105 A1 | 5/2003 | Krich et al. |
| 2005/0009865 A1 | 1/2005 | Kudo et al. |
| 2005/0014697 A1 | 1/2005 | Stamler et al. |
| 2005/0187166 A1 | 8/2005 | Stamler et al. |
| 2005/0260126 A1 | 11/2005 | Kudo et al. |
| 2006/0018825 A1 | 1/2006 | Kudo et al. |
| 2007/0054903 A1 | 3/2007 | Kim et al. |
| 2007/0293492 A1 | 12/2007 | DeVita et al. |
| 2008/0103308 A1 | 5/2008 | Ragini et al. |
| 2009/0029987 A1 | 1/2009 | Wong et al. |
| 2010/0035887 A1 | 2/2010 | Ricciardi |
| 2010/0113508 A1 | 5/2010 | Binch et al. |
| 2010/0144733 A1 | 6/2010 | Doyle et al. |
| 2010/0204234 A1 | 8/2010 | Hartmann et al. |
| 2010/0286174 A1 | 11/2010 | Stamler et al. |
| 2013/0178499 A1 | 7/2013 | Sun et al. |
| 2013/0261122 A1 | 10/2013 | Sun et al. |
| 2013/0261123 A1 | 10/2013 | Sun et al. |
| 2014/0094465 A1 | 4/2014 | Sun et al. |
| 2014/0329821 A1 | 11/2014 | Sun et al. |
| 2015/0080429 A1 | 3/2015 | Sun et al. |
| 2015/0183774 A1 | 7/2015 | Sun et al. |
| 2015/0336897 A1 | 11/2015 | Sun et al. |
| 2016/0067254 A1 | 3/2016 | Sun et al. |
| 2016/0220556 A1 | 8/2016 | Sun et al. |
| 2016/0279117 A1 | 9/2016 | Sun et al. |
| 2016/0340312 A1 | 11/2016 | Sun et al. |

FOREIGN PATENT DOCUMENTS

| | | |
|---|---|---|
| CN | 101068551 A | 11/2007 |
| EP | 0058822 | 9/1982 |
| EP | 1277738 A1 | 1/2003 |
| EP | 1683523 A1 | 7/2006 |
| JP | 2007-504281 A | 3/2007 |
| JP | 2008-521905 A | 6/2008 |
| JP | 2013-519680 A | 5/2013 |
| WO | WO 1997-48694 | 12/1997 |

(Continued)

OTHER PUBLICATIONS

Bateman et al. (Sep. 29, 2008) "Human carbonyl reductase is an S-nitrosoglutathione reductase" J Biol Chem, 283 p. 35756-35762.
Bowman et al. (2007) J. Am. Chem Soc. 129:3634-3640 "Protein Flexibility and Species Specificity in Structure-Based Drug Discovery: Dihydrofolate Reductase as a Test System" with Supplement pp. S2-S34.
Branchini, B et al, (1989) "Naphthyl- and Quinolylluciferin: Green and Red Light Emitting Firefly Luciferin Analogues" Photochemistry and Photobiology, 49(5), 689-95.
Bridges et al. (1968) "The Fluorescence of Indoles and Analine Derivatives" Biochem. J. 107:225-237.

(Continued)

*Primary Examiner* — Alicia L Otton
(74) *Attorney, Agent, or Firm* — Lihua Zheng

(57) ABSTRACT

The present invention provides solid forms and compositions thereof, which are useful as an inhibitor of S-nitrosoglutathione reductase and which exhibit desirable characteristics for the same.

16 Claims, 14 Drawing Sheets

(56) References Cited

FOREIGN PATENT DOCUMENTS

| WO | WO 1998-54158 | 12/1998 |
| --- | --- | --- |
| WO | WO 1999-38845 | 8/1999 |
| WO | WO 01/083456 | 11/2001 |
| WO | WO 2002-028841 | 4/2002 |
| WO | WO 2002-060876 | 8/2002 |
| WO | WO 2003-016292 | 2/2003 |
| WO | WO 2004-080170 | 9/2004 |
| WO | WO 2004/103973 A1 | 12/2004 |
| WO | WO 2005-063712 | 7/2005 |
| WO | WO 2005-118580 | 12/2005 |
| WO | WO 2006-004722 | 1/2006 |
| WO | WO 2006-034491 A2 | 3/2006 |
| WO | WO 2006-060390 A1 | 6/2006 |
| WO | WO 2006-127329 | 11/2006 |
| WO | WO 2006-130551 | 12/2006 |
| WO | WO 2007-016525 A2 | 2/2007 |
| WO | WO 2008-032105 | 3/2008 |
| WO | WO 2008-069976 | 6/2008 |
| WO | WO 2008-144865 | 12/2008 |
| WO | WO 2008-157500 | 12/2008 |
| WO | WO 2009-007457 | 1/2009 |
| WO | WO 2009-076665 | 6/2009 |
| WO | WO 2010-018458 | 2/2010 |
| WO | WO 2010-019903 A1 | 2/2010 |
| WO | WO 2010-019905 A1 | 2/2010 |
| WO | WO 2010-019909 A1 | 2/2010 |
| WO | WO 2010-107476 | 9/2010 |
| WO | WO 2011-100433 A1 | 8/2011 |
| WO | WO 2012-048181 | 4/2012 |
| WO | WO 2012-083165 | 6/2012 |
| WO | WO 2012-083171 | 6/2012 |
| WO | WO 2012-170371 | 12/2012 |

OTHER PUBLICATIONS

De Belder et al. (May 1994) "Effects of S-nitroso-glutathione in the human forearm circulation; evidence for selective inhibition of platelet activation", Cardiovasc Res., 28(5):691-694.

de Jesus-Berrios et al. (Nov. 2003) "Enzymes that Counteract Nitrosative Stress Promot Fungal Virulence", Curr. Biol., 13:1963-1968.

EP Search Report dated Jun. 18, 2015 in EP application serial No. EP 11849278.4.

EP Search Report dated Jun. 26, 2014 in EP application serial No. 11831651.2.

EP Search Report dated Nov. 19, 2015 in EP application serial No. EP 15180449.9.

Foster et al. (Apr. 2003) "S-nitrosylation in health and disease", Trends in Molecular Medicine, 9(4):160-168.

Frotscher et al. (2008) "Design, Synthesis, and Biological Evaluation of (Hydroxyphenyl)naphthalene and -quinoline Derivatives: Potent and Selective Nonsteroidal Inhibitors of 17β-Hydroxysteroid Dehydrogenase Type 1 (17β-HSD1) for the Treatment of Estrogen-Dependent Diseases ", J. Med. Che. 51(7):2158-2169.

Gaston et al. (Dec. 1993) "Endogenous nitrogen oxides and bronchodilator S-nitrosothiols in human airways", Proc. Natl. Acad. Sci. USA, 90:10957-10961.

Georgii et al. (2011) "Topical S-nitrosoglutathione-Releasing Hydrogel Improves Healing of Rat Ischaemic Wounds", J Tissue Eng Regen Med, 5:612-619.

Haq et al. (2007) "S-nitrosoglutathione Prevents Interphotoreceptor Retinoid-Binding Protein (IRBP[161-180]) Induced Experimental Autoimmune Uveitis" J Ocular Pharm and Therapeutics, 23(3):221-231.

International Preliminary Report on Patentability mailed in PCT/US2011/055200 dated Apr. 18, 2013.

International Preliminary Report on Patentability mailed in PCT/US2011/065490 dated Jun. 27, 2013.

International Preliminary Report on Patentability from PCT/US2016/050974 dated Mar. 22, 2018.

International Search Report and Written Opinion mailed in PCT/US2011/055200 dated Mar. 16, 2012.

International Search Report and Written Opinion mailed in PCT/US2011/065490 dated May 2, 2012.

International Search Report and Written Opinion from PCT/US2016/050974 dated Nov. 29, 2016.

Jensen et al. (1998) "S-Nitrosoglutathione is a substrate for rat alcohol dehydrognease class III isoenzyme", Biochem J., 331:659-668.

Kaposzta et al. (2002) "S-Nitrosoglutathione Reduces Asymptomatic Embolization After Carotid Angioplasty", Circulation,106(24):3057-3062.

Kouznetsov et al.. (2005) "Recent Progress in the Synthesis of Quinolines" Current Organic Chemistry 9:141-161.

Lee (2008), "Acetaminophen-related Acute Liver Failure in the United States" Hepatology Research, 38 (Suppl. 1): S3-S8.

Lima et al. (2010), "S-Nitrosylation in Cardiovascular Signaling", Circ Res. 106(4):633-646.

Lipton et al. (Sep. 2001) "S-Nitrosothiols signal the ventilatory response to hypoxia", Nature, 413:171-174.

Liu et al. (Feb. 2004) "Essential Roles of S-Nitrosothiols in Vascular Homeostatsis and Endotoxic Shock", Cell, 116(4):617-628.

Liu et al. (Mar. 2001) "A metabolic enzyme for S-nitrosothiol conserved from bacterial to humans", Nature, 410:490-494.

Madapa et al (2008) "Advances in the synthesis of quinoline and quinoline-annulated ring systems" Current Organic Chemistry 12:1116-1183.

Mphahlele (Jan. 2010) "Synthesis of 2-Arylquinolin-4(1H)-ones and Their Transformation to N-Alkylated and O-Alkylated Derivatives" Journal of Heterocyclic Chemistry 43(2):255-260.

Prince et al. (2010) "The Nitric Oxide Donor S-Nitrosoglutathione Reduces Apoptotic Primary Liver Cell Loss in a Three-Dimensional Perfusion Bioreactor Culture Model Developed for Liver Support" Tissue Eng 16(3):861-866.

Que et al. (Jun. 2005) "Protection from Experimental Asthma by an Endogenous Bronchodilator", Science, 308(5728):1618-1621.

Sandelier (2008); downloaded from the internet: http://www.dtic.mil/gni-bin/GetTRDoc?AD=ADA486097&Location=U2&doc=GetTRDoc.pdf on Feb. 13, 2012) Tandem reduction cyclization of 0-nitrophenyl propargyl alcohols—A novel synthesis of 2- & 2,4-disubstituted quinolines and application to the synthesis of streponigrim, UMI No. 3324767.

Sanghani et al. (2000) "Kinetic Mechanism of Human Glutathioone-Dependent Formaldehyde Dehydrogenase", Biochemistry,39:10720-10729.

Sanghani et al. (2002) "Human Glutathione-Dependent Formaldehyde Dehydrognease. Structures of Apo, Binary, and Inhibitory Ternary Complexes", Biochemistry,41:10778-10786.

Sanghani et al. (Jul. 11, 2009) Kinetic and Cellular Characterization of Novel Inhibitors of S-Nitrosogluthathione Reductase, J. Biol. Chem. 284:24354-24362.

Silverman et al. (2004) "The Organic Chemistry of Drug Design and Drug Action "Elsevier pp. 29-32.

Smith et al. (1955) "Studies in detoxication. 65. The metabolism of quinoline. New metabolites of quinoline, with observations on the metabolism of 3-, 5-, and 6-hydroxyquinoline and 2,4-dihydroxyquinoline" Biochem. J. 60(2)284-290.

Staab et al. (2008) "Dual functions of alcohol dehydrogenase 3: implications with focus on formaldehyde dehydrogenase and S-nitroglutathione reductase activities", Cell Mol. Life Sci, 65:3950-3960.

Staab et al. (Jun. 15, 2009) "Medium-chain fatty acids and glutathione derivatives as inhibitors of S-nitrosoglutathione reduction mediated by alcohol dehydrogenase 3", Chemico-Biological Interactions 180(1):113-118.

Stamler et al. (Aug. 1992) "Nitric oxide circulates in mammalian plasma primarily as an S-nitrose adduct of serium albumin", Proc. Natl. Acad. Sci. USA, 89:7674-7677.

Tanaka et al. (2002) "Crystal Structure of Formaldehyde Dehydrogenase from Pseudomonas putida: the Structural Origin of the Tightly Bound Cofactor in Nicotinoprotein Dehydrogenases" J. Mol. Biol. 324:519-533.

(56) References Cited

OTHER PUBLICATIONS

Uotila and Koivusalo (1989) Coenzymes and Cofactors vol. 3: Glutathione, part A., D. Dolphin, ed. pp. 517-551 (New York, John Wiley & Sons).

Zaman et al. (2001) "S-Nitrosoglutathione Increases Cystic Fibrosis Transmembrane Regulator Maturation", *Biochem Biophys Res Commun.*, 284:65-70.

SOLID FORMS OF AN S-NITROSOGLUTATHIONE REDUCTASE INHIBITOR

RELATED APPLICATIONS

This application is a National Stage Entry of PCT International Application Ser. No. PCT/US2016/050974, filed Sep. 9, 2016. PCT International Application Ser. No. PCT/US2016/050974 claims priority to U.S. Provisional Application Ser. No. 62/216,765, filed Sep. 10, 2015, entitled "Solid Forms of an S-Nitrosoglutathione Reductase Inhibitor." Each of the above-referenced applications are incorporated herein in their entirety by reference.

FIELD OF THE INVENTION

The present invention provides solid forms of a compound useful as an inhibitor of S-nitrosoglutathione reductase (GSNOR). The invention also provides pharmaceutically acceptable compositions comprising solid forms of the present invention and methods of using the compositions in the treatment of various disorders.

BACKGROUND

The chemical compound nitric oxide is a gas with chemical formula NO. NO is one of the few gaseous signaling molecules known in biological systems, and plays an important role in controlling various biological events. For example, the endothelium uses NO to signal surrounding smooth muscle in the walls of arterioles to relax, resulting in vasodilation and increased blood flow to hypoxic tissues. NO is also involved in regulating smooth muscle proliferation, platelet function, and neurotransmission, and plays a role in host defense. Although NO is highly reactive and has a lifetime of a few seconds, it can both diffuse freely across membranes and bind to many molecular targets. These attributes make NO an ideal signaling molecule capable of controlling biological events between adjacent cells and within cells.

NO is a free radical gas, which makes it reactive and unstable, thus NO is short lived in vivo, having a half life of 3-5 seconds under physiologic conditions. In the presence of oxygen, NO can combine with thiols to generate a biologically important class of stable NO adducts called S-nitrosothiols (SNO's). This stable pool of NO has been postulated to act as a source of bioactive NO and as such appears to be critically important in health and disease, given the centrality of NO in cellular homeostasis (Stamler et al., Proc. Natl. Acad. Sci. USA, 89:7674-7677 (1992)). Protein SNO's play broad roles in the function of cardiovascular, respiratory, metabolic, gastrointestinal, immune, and central nervous system (Foster et al., Trends in Molecular Medicine, 9 (4):160-168, (2003)). One of the most studied SNO's in biological systems is S-nitrosoglutathione (GSNO) (Gaston et al., Proc. Natl. Acad. Sci. USA 90:10957-10961 (1993)), an emerging key regulator in NO signaling since it is an efficient trans-nitrosating agent and appears to maintain an equilibrium with other S-nitrosated proteins (Liu et al., Nature, 410:490-494 (2001)) within cells. Given this pivotal position in the NO-SNO continuum, GSNO provides a therapeutically promising target to consider when NO modulation is pharmacologically warranted.

In light of this understanding of GSNO as a key regulator of NO homeostasis and cellular SNO levels, studies have focused on examining endogenous production of GSNO and SNO proteins, which occurs downstream from the production of the NO radical by the nitric oxide synthetase (NOS) enzymes. More recently there has been an increasing understanding of enzymatic catabolism of GSNO which has an important role in governing available concentrations of GSNO and consequently available NO and SNO's.

Central to this understanding of GSNO catabolism, researchers have recently identified a highly conserved S-nitrosoglutathione reductase (GSNOR) (Jensen et al., Biochem J., 331:659-668 (1998); Liu et al., (2001)). GSNOR is also known as glutathione-dependent formaldehyde dehydrogenase (GSH-FDH), alcohol dehydrogenase 3 (ADH-3) (Uotila and Koivusalo, Coenzymes and Cofactors, D. Dolphin, ed. pp. 517-551 (New York, John Wiley & Sons, (1989)), and alcohol dehydrogenase 5 (ADH-5). Importantly GSNOR shows greater activity toward GSNO than other substrates (Jensen et al., (1998); Liu et al., (2001)) and appears to mediate important protein and peptide denitrosating activity in bacteria, plants, and animals. GSNOR appears to be the major GSNO-metabolizing enzyme in eukaryotes (Liu et al., (2001)). Thus, GSNO can accumulate in biological compartments where GSNOR activity is low or absent (e.g., airway lining fluid) (Gaston et al., (1993)).

Yeast deficient in GSNOR accumulate S-nitrosylated proteins which are not substrates of the enzyme, which is strongly suggestive that GSNO exists in equilibrium with SNO-proteins (Liu et al., (2001)). Precise enzymatic control over ambient levels of GSNO and thus SNO-proteins raises the possibility that GSNO/GSNOR may play roles across a host of physiological and pathological functions. Indeed, GSNO specifically has been implicated in physiologic processes ranging from the drive to breathe (Lipton et al., Nature, 413:171-174 (2001)) to regulation of the cystic fibrosis transmembrane regulator (Zaman et al., Biochem Biophys Res Commun, 284:65-70 (2001)), to regulation of vascular tone, thrombosis, and platelet function (de Belder et al., Cardiovasc Res.; 28(5):691-4 (1994)), Z. Kaposzta, et al., Circulation; 106(24): 3057-3062, (2002)) as well as host defense (de Jesus-Berrios et al., Curr. Biol., 13:1963-1968 (2003)).

Collectively, data suggest GSNO as a primary physiological ligand for the enzyme S-nitrosoglutathione reductase (GSNOR), which catabolizes GSNO and consequently reduces available SNO's and NO in biological systems (Liu et al., (2001)), (Liu et al., Cell, 116(4), 617-628 (2004)), and (Que et al., Science, 308, (5728):1618-1621 (2005)). As such, this enzyme plays a central role in regulating local and systemic bioactive NO. Since perturbations in NO bioavailability has been linked to the pathogenesis of numerous disease states, including cystic fibrosis, hypertension, atherosclerosis, thrombosis, asthma, gastrointestinal disorders, inflammation, and cancer, agents that regulate GSNOR activity are candidate therapeutic agents for treating diseases associated with NO imbalance.

Nitric oxide (NO), S-nitrosoglutathione (GSNO), and S-nitrosoglutathione reductase (GSNOR) regulate normal lung physiology and contribute to lung pathophysiology. Under normal conditions, NO and GSNO maintain normal lung physiology and function via their modulatory effects on the cystic fibrosis transmembrane regulator (CFTR), anti-inflammatory, and bronchodilatory actions. Lowered levels of these mediators in pulmonary diseases such as cystic fibrosis, asthma, and chronic obstructive pulmonary disease (COPD) may occur via up-regulation of GSNOR enzyme activity. These lowered levels of NO and GSNO, and thus lowered CFTR function and anti-inflammatory capabilities, are key events that contribute to pulmonary diseases and which can potentially be reversed via GSNOR inhibition.

S-nitrosoglutathione (GSNO) has been shown to promote repair and/or regeneration of mammalian organs, such as the heart (Lima et al., 2010), blood vessels (Lima et al., 2010), skin (Georgii et al., 2010), eye or ocular structures (Haq et al., 2007) and liver (Prince et al., 2010). S-nitrosoglutathione reductase (GSNOR) is the major catabolic enzyme of GSNO. Inhibition of GSNOR is thought to increase endogenous GSNO.

Inflammatory bowel diseases (IBD's), including Crohn's and ulcerative colitis, are chronic inflammatory disorders of the gastrointestinal (GI) tract, in which NO, GSNO, and GSNOR can exert influences. Under normal conditions, NO and GSNO function to maintain normal intestinal physiology via anti-inflammatory actions and maintenance of the intestinal epithelial cell barrier. In IBD, reduced levels of GSNO and NO are evident and likely occur via up-regulation of GSNOR activity. The lowered levels of these mediators contribute to the pathophysiology of IBD via disruption of the epithelial barrier via dysregulation of proteins involved in maintaining epithelial tight junctions. This epithelial barrier dysfunction, with the ensuing entry of microorganisms from the lumen, and the overall lowered anti-inflammatory capabilities in the presence of lowered NO and GSNO, are key events in IBD progression that can be potentially influenced by targeting GSNOR.

Cystic fibrosis (CF) is one of the most common lethal genetic diseases in Caucasians. Approximately one in 3,500 children in the US is born with CF each year. It is a disease that affects all racial and ethnic groups, but is more common among Caucasians. An estimated 30,000 American adults and children have CF, and the median predicted age of survival is 37.4 years (CFF Registry Report 2007, Cystic Fibrosis Foundation, Bethesda, Md.). CF is an autosomal recessive hereditary disease caused by a mutation in the gene for the cystic fibrosis transmembrane regulator (CFTR) protein. More than 1,000 disease-associated mutations have been discovered in the CFTR gene with the most common mutation being a deletion of the amino acid phenylalanine at position 508 (F508del). The CFTR protein is located on the apical membrane and is responsible for chloride transport across epithelial cells on mucosal surfaces. GSNO has been identified as a positive modulator of CFTR. As GSNOR is the primary catabolizing enzyme of GSNO, it is hypothesized that inhibition of GSNOR may improve F508del-CFTR function via nitrosation of chaperone proteins, prevention of CFTR proteosomal degradation, promotion of CFTR maturation, and maintenance of epithelial tight junctions. Currently there is no curative treatment for CF; therefore, new therapies are needed for the disease.

Cell death is the crucial event leading to clinical manifestation of hepatotoxicity from drugs, viruses and alcohol. Glutathione (GSH) is the most abundant redox molecule in cells and thus the most important determinant of cellular redox status. Thiols in proteins undergo a wide range of reversible redox modifications during times of exposure to reactive oxygen and reactive nitrogen species, which can affect protein activity. The maintenance of hepatic GSH is a dynamic process achieved by a balance between rates of GSH synthesis, GSH and GSSG efflux, GSH reactions with reactive oxygen species and reactive nitrogen species and utilization by GSH peroxidase. Both GSNO and GSNOR play roles in the regulation of protein redox status by GSH.

Acetaminophen overdoses are the leading cause of acute liver failure (ALF) in the United States, Great Britain and most of Europe. More than 100,000 calls to the U.S. Poison Control Centers, 56,000 emergency room visits, 2600 hospitalizations, nearly 500 deaths are attributed to acetaminophen in this country annually. Approximately, 60% recover without needing a liver transplant, 9% are transplanted and 30% of patients succumb to the illness. The acetaminophen-related death rate exceeds by at least three-fold the number of deaths due to all other idiosyncratic drug reactions combined (Lee, *Hepatol Res* 2008; 38 (Suppl. 1):S3-S8).

Liver transplantation has become the primary treatment for patients with fulminant hepatic failure and end-stage chronic liver disease, as well as certain metabolic liver diseases. Thus, the demand for transplantation now greatly exceeds the availability of donor organs. It has been estimated that more than 18 000 patients are currently registered with the United Network for Organ Sharing (UNOS) and that an additional 9000 patients are added to the liver transplant waiting list each year, yet less than 5000 cadaveric donors are available for transplantation.

Currently, there is a great need in the art for diagnostics, prophylaxis, ameliorations, and treatments for medical conditions where there is a need for increased NO bioactivity. In addition, there is a significant need for novel compounds, compositions, and methods for preventing, ameliorating, or reversing NO-associated disorders. The compound 3-chloro-4-(6-hydroxyquinolin-2-yl)benzoic acid (Compound 1) is disclosed in International PCT Publication WO2012/048181 as an inhibitor of GSNOR and thus as a useful treatment for NO related diseases such as cystic fibrosis, asthma, COPD, IBD, etc. It would be desirable to provide a solid form of Compound 1 that, as compared to Compound 1, imparts characteristics such as improved aqueous solubility, stability and/or ease of formulation. Accordingly, the present invention provides several solid forms.

SUMMARY OF THE INVENTION

It has now been found that the novel solid forms of the present invention, and compositions thereof, are useful as inhibitors of S-nitrosoglutathione reductase and exhibit desirable characteristics for the same. In general, these solid forms, and pharmaceutically acceptable compositions thereof, are useful for treating or lessening the severity of a variety of diseases or disorders as described in detail herein.

DETAILED DESCRIPTION OF THE INVENTION

Figure 1:
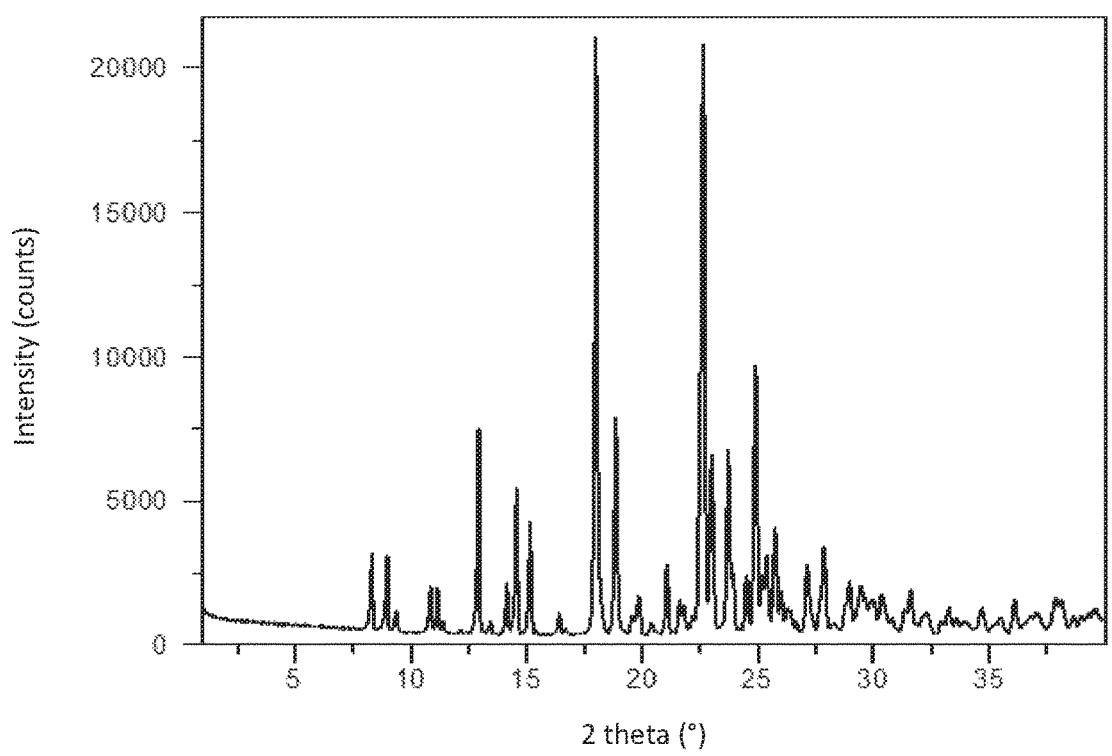
FIG. 1 depicts the x-ray powder diffraction (XRPD) pattern for Form A of Compound 1.

General Description of Certain Aspects of the Invention

International PCT Publication WO2012/048181 ("the '181 application"), with the filing date of Oct. 7, 2011, the entirety of which is hereby incorporated herein by reference, describes certain quinolone compounds which selectively and reversibly inhibit the activity of S-nitrosoglutathione reductase. Such compounds include Compound 1:

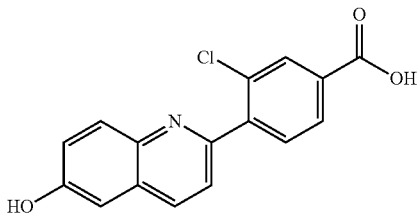 [SMILES: O=C(O)c1ccc(-c2ccc3cc(O)ccc3n2)c(Cl)c1]

Compound 1, 3-chloro-4-(6-hydroxyquinolin-2-yl)benzoic acid, is designated as compound number 8 in the '181 application and the synthesis of Compound 1 is described in detail at Example 8 of the '181 application.

Compound 1 is active in a variety of assays and therapeutic models demonstrating selective and reversible inhibition of S-nitrosoglutathione reductase (GSNOR). Notably, Compound 1 demonstrates efficacy in asthma, COPD, cystic fibrosis, and IBD models (described in international PCT Publication WO2012/048181; U.S. application 62/061,557; U.S. application 62/093,712; U.S. application 62/138,792 and U.S. application 62/209,724, and PCT publication WO 2016/057811). Accordingly, Compound 1 is useful for treating one or more disorders associated with activity of GSNOR.

It would be desirable to provide a solid form of Compound 1 that, as compared to Compound 1, imparts characteristics such as improved aqueous solubility, stability and/or ease of formulation. Accordingly, the present invention provides several solid forms of Compound 1.

According to one embodiment, the present invention provides an amorphous form, a crystalline form, or a mixture thereof. Exemplary solid forms are described in more detail below.

In other embodiments, the present invention provides Compound 1 substantially free of impurities. As used herein, the term "substantially free of impurities" means that the compound contains no significant amount of extraneous matter. Such extraneous matter may include starting materials, residual solvents, or any other impurities that may result from the preparation of, and/or isolation of, Compound 1. In certain embodiments, at least about 90% by weight of Compound 1 is present. In certain embodiments, at least about 95% by weight of Compound 1 is present. In still other embodiments of the invention, at least about 99% by weight of Compound 1 is present.

According to one embodiment, Compound 1 contains no more than about 5.0 area percent HPLC of total organic impurities and, in certain embodiments, no more than about 3.0 area percent HPLC of total organic impurities and, in certain embodiments, no more than about 1.5 area percent HPLC total organic impurities relative to the total area of the HPLC chromatogram. In other embodiments, Compound 1 contains no more than about 1.0 area percent HPLC of any single impurity; no more than about 0.7 area percent HPLC of any single impurity, and, in certain embodiments, no more than about 0.5 area percent HPLC of any single impurity, relative to the total area of the HPLC chromatogram.

The structure depicted for Compound 1 is also meant to include all tautomeric forms of Compound 1. Additionally, structures depicted here are also meant to include compounds that differ only in the presence of one or more isotopically enriched atoms. For example, compounds having the present structure except for the replacement of hydrogen by deuterium or tritium, or the replacement of a carbon by a $^{13}$C- or $^{14}$C-enriched carbon are within the scope of this invention.

Solid Forms of Compound 1:

It has been found that Compound 1 can exist in a variety of solid forms. Such forms include polymorphs and amorphous forms. The solid forms can be solvates, hydrates and unsolvated forms of Compound 1. All such forms are contemplated by the present invention. In certain embodiments, the present invention provides Compound 1 as a mixture of one or more solid forms of Compound 1.

As used herein, the term "polymorph" refers to the different crystal structures (of solvated or unsolvated forms) in which a compound can crystallize.

As used herein, the term "solvate" refers to a solid form with either a stoichiometric or non-stoichiometric amount of solvent (e.g., a channel solvate). For polymorphs, the solvent is incorporated into the crystal structure. Similarly, the term "hydrate" refers to a solid form with either a stoichiometric or non-stoichiometric amount of water. The term "hemi-hydrate" refers to a solid form with about 1 equivalent of water relative to 2 equivalents of anhydrous Compound 1 in the crystal structure. For polymorphs, the water is incorporated into the crystal structure.

As used herein, the term "about", when used in reference to a degree 2-theta value refers to the stated value±0.3 degree 2-theta. In certain embodiments, "about" refers to ±0.2 degree 2-theta or ±0.1 degree 2-theta. In certain embodiments, "about" refers to ±0.2 degree 2-theta.

In certain embodiments, Compound 1 is a crystalline solid. In other embodiments, Compound 1 is a crystalline solid substantially free of amorphous Compound 1. As used herein, the term "substantially free of amorphous Compound 1" means that the compound contains no significant amount of amorphous Compound 1. In certain embodiments, at least about 90% by weight of crystalline Compound 1 is present, or at least about 95% by weight of crystalline Compound 1 is present. In still other embodiments of the invention, at least about 97%, 98% or 99% by weight of crystalline compound 1 is present.

In certain embodiments, Compound 1 is a hydrate polymorphic form. In one embodiment, the present invention provides a hemi-hydrate polymorphic form of Compound 1 referred to herein as Form A.

In certain embodiments, Compound 1 is a neat or unsolvated crystal form and thus does not have any water or solvent incorporated into the crystal structure. In one embodiment, the present invention provides an anhydrous polymorphic form of Compound 1 referred to herein as Form B.

In certain embodiments, Compound 1 is a hemi-hydrate. In certain embodiments, the hemi-hydrate of the present invention provides Form A of Compound 1. Form A of Compound 1 is also known as Form III of Compound 1.

According to another embodiment, Form A of Compound 1 is characterized by one or more peaks in its powder X-ray diffraction pattern selected from those at about 12.92, about 18.01, about 18.86, about 22.63, about 23.00, about 23.72, and about 24.88 degrees 2-theta. In some embodiments, Form A of Compound 1 is characterized by two or more peaks in its powder X-ray diffraction pattern selected from those at about 12.92, about 18.01, about 18.86, about 22.63, about 23.00, about 23.72, and about 24.88 degrees 2-theta. In certain embodiments, Form A of Compound 1 is characterized by three or more peaks in its powder X-ray diffraction pattern selected from those at about 12.92, about 18.01, about 18.86, about 22.63, about 23.00, about 23.72, and about 24.88 degrees 2-theta. For example, in one embodiment, Form A of Compound 1 is characterized by a peak in its powder X-ray diffraction pattern at about 12.92. In another example, Form A of Compound 1 is characterized by peaks in its powder X-ray diffraction pattern at about 12.92 and one or more additional peaks selected from those at about 18.01, about 18.86, about 22.63, about 23.00, about 23.72, and about 24.88 degrees 2-theta. In another example, Form A of Compound 1 is characterized by peaks in its powder X-ray diffraction pattern at about 12.92 and two or more additional peaks selected from those at about 18.01, about 18.86, about 22.63, about 23.00, about 23.72, and about 24.88 degrees 2-theta. In another example, Form A of Compound 1 is characterized by peaks in its powder X-ray diffraction pattern at about 12.92 and three or more additional peaks selected from those at about 18.01, about 18.86, about 22.63, about 23.00, about 23.72, and about 24.88 degrees 2-theta. In another example, Form A of Compound 1 is characterized by peaks in its powder X-ray diffraction pattern at about 12.92 and four or more additional peaks selected from those at about 18.01, about 18.86, about 22.63, about 23.00, about 23.72, and about 24.88 degrees 2-theta. In another example, Form A of Compound 1 is characterized by peaks in its powder X-ray diffraction pattern at about 12.92 and about 18.01, and optionally one or more additional peaks selected from about 18.86, about 22.63, about 23.00, about 23.72, and about 24.88 degrees 2-theta. In another example, Form A of Compound 1 is characterized by peaks in its powder X-ray diffraction pattern at about 12.92, about 18.01, and about 22.63, and optionally one or more additional peaks selected from about 18.86, about 23.00, about 23.72, and about 24.88 degrees 2-theta. In another example, Form A of Compound 1 is characterized by peaks in its powder X-ray diffraction pattern at about 12.92, about 18.01, about 22.63, and about 24.88, and optionally one or more additional peaks selected from about 18.86, about 23.00, and about 23.72. In another example, Form A of Compound 1 is characterized by peaks in its powder X-ray diffraction pattern at about 12.92, about 18.01, about 18.86, about 22.63, about 23.00, about 23.72, and about 24.88 degrees 2-theta. In another embodiment, Form A of Compound 1 is characterized by having one or more peaks in its X-ray powder diffraction pattern selected from the group consisting of at about 8.32, 8.97, 12.92, 14.56, 15.14, 18.01, 18.86, 22.63, 23.00, 23.72 and 24.88 degrees 2-theta. In particular embodiments, Form A of Compound 1 is characterized by all or substantially all of the peaks in its X-ray powder diffraction pattern selected from those at about 8.32, 8.97, 12.92, 14.56, 15.14, 18.01, 18.86, 22.63, 23.00, 23.72 and 24.88 degrees 2-theta. In an exemplary embodiment, Form A of Compound 1 is characterized by all or substantially all of the peaks in its X-ray powder diffraction pattern selected from those at about:

| °2θ |
|---|
| 8.32 |
| 8.97 |
| 9.39 |
| 10.85 |
| 11.15 |
| 11.38 |
| 12.16 |
| 12.92 |
| 13.44 |
| 14.14 |
| 14.56 |
| 15.14 |
| 16.43 |
| 16.70 |
| 18.01 |
| 18.86 |
| 19.57 |
| 19.85 |
| 20.42 |
| 21.06 |
| 21.62 |
| 21.80 |
| 22.18 |
| 22.63 |
| 23.00 |
| 23.72 |
| 23.91 |
| 24.49 |
| 24.88 |
| 25.18 |
| 25.37 |
| 25.73 |
| 26.01 |
| 26.29 |
| 26.64 |
| 27.12 |
| 27.87 |
| 28.27 |
| 28.97 |
| 29.46 |

According to another embodiment, Form A of Compound 1 is characterized by one or more peaks in its powder X-ray diffraction pattern selected from those at about 12.9, about 18.0, about 18.9, about 22.6, about 23.0, about 23.7, and about 24.9 degrees 2-theta. In some embodiments, Form A of Compound 1 is characterized by two or more peaks in its powder X-ray diffraction pattern selected from those at about 12.9, about 18.0, about 18.9, about 22.6, about 23.0, about 23.7, and about 24.9 degrees 2-theta. In certain embodiments, Form A of Compound 1 is characterized by three or more peaks in its powder X-ray diffraction pattern selected from those at about 12.9, about 18.0, about 18.9, about 22.6, about 23.0, about 23.7, and about 24.9 degrees 2-theta. For example, in one embodiment, Form A of Compound 1 is characterized by a peak in its powder X-ray diffraction pattern at about 12.9. In another example, Form A of Compound 1 is characterized by peaks in its powder X-ray diffraction pattern at about 12.9 and one or more additional peaks selected from those at about 18.0, about 18.9, about 22.6, about 23.0, about 23.7, and about 24.9 degrees 2-theta. In another example, Form A of Compound 1 is characterized by peaks in its powder X-ray diffraction pattern at about 12.9 and two or more additional peaks in its powder X-ray diffraction pattern selected from those at about 18.0, about 18.9, about 22.6, about 23.0, about 23.7, and about 24.9 degrees 2-theta. In another example, Form A of Compound 1 is characterized by peaks in its powder X-ray diffraction pattern at about 12.9 and three or more additional peaks in its powder X-ray diffraction pattern selected from those at about 18.0, about 18.9, about 22.6, about 23.0, about 23.7, and about 24.9 degrees 2-theta. In another example, Form A of Compound 1 is characterized by peaks in its powder X-ray diffraction pattern at about 12.9 and four or more additional peaks in its powder X-ray diffraction pattern selected from those at about 18.0, about 18.9, about 22.6, about 23.0, about 23.7, and about 24.9 degrees 2-theta. In another example, Form A of Compound 1 is characterized by peaks in its powder X-ray diffraction pattern at about 12.9 and about 18.0, and optionally one or more additional peaks selected from about 18.9, about 22.6, about 23.0, about 23.7, and about 24.9 degrees 2-theta. In another example, Form A of Compound 1 is characterized by peaks in its powder X-ray diffraction pattern at about 12.9, about 18.0, and about 22.6, and optionally one or more additional peaks selected from about 18.9, about 23.0, about 23.7, and about 24.9 degrees 2-theta. In another example, Form A of Compound 1 is characterized by peaks in its powder X-ray diffraction pattern at about 12.9, about 18.0, about 22.6, and about 24.9, and optionally one or more additional peaks selected from about 18.9, about 23.0, and about 23.7. In another example, Form A of Compound 1 is characterized by peaks in its powder X-ray diffraction pattern at about 12.9, about 18.0, about 18.9, about 22.6, about 23.0, about 23.7, and about 24.9 degrees 2-theta. In another embodiment, Form A of Compound 1 is characterized by having one or more peaks in its X-ray powder diffraction pattern selected from the group consisting of at about 8.3, 9.0, 12.9, 14.6, 15.1, 18.0, 18.9, 22.6, 23.0, 23.7 and 24.9 degrees 2-theta. In particular embodiments, Form A of Compound 1 is characterized by all or substantially all of the peaks in its X-ray powder diffraction pattern selected from those at about 8.3, 9.0, 12.9, 14.6, 15.1, 18.0, 18.9, 22.6, 23.0, 23.7 and 24.9 degrees 2-theta. In an exemplary embodiment, Form A of Compound 1 is characterized by all or substantially all of the peaks in its X-ray powder diffraction pattern selected from those at about:

| °2θ |
|---|
| 8.3 |
| 9.0 |
| 9.4 |
| 10.9 |
| 11.2 |
| 11.4 |
| 12.2 |
| 12.9 |
| 13.4 |
| 14.1 |
| 14.6 |
| 15.1 |
| 16.4 |
| 16.7 |
| 18.0 |
| 18.9 |
| 19.6 |
| 19.9 |
| 20.4 |
| 21.1 |
| 21.6 |
| 21.8 |
| 22.2 |
| 22.6 |
| 23.0 |

-continued

| °2θ |
|---|
| 23.7 |
| 23.9 |
| 24.5 |
| 24.9 |
| 25.2 |
| 25.4 |
| 25.7 |
| 26.0 |
| 26.3 |
| 26.6 |
| 27.1 |
| 27.9 |
| 28.3 |
| 29.0 |
| 29.5 |

According to one aspect, Form A of Compound 1 has a powder X-ray diffraction pattern substantially similar to that depicted in FIG. 1. According to another aspect, Form A of Compound 1 has a thermogravimetric analysis pattern substantially similar to that depicted in FIG. 2. Accordingly to yet another aspect, Form A of Compound 1 has a differential scanning calorimetry pattern substantially similar to that depicted in FIG. 3. According to a further embodiment, Form A of Compound 1 has a $^1$H NMR spectrum substantially similar to that depicted in FIG. 4. Form A of Compound 1 can be characterized by substantial similarity to two or more of these figures simultaneously.

In certain embodiments, the present invention provides an unsolvated, anhydrous crystalline form, Form B of Compound 1. Form B of Compound 1 is also known as Form IV of Compound 1.

According to another embodiment, Form B of Compound 1 is characterized by one or more peaks in its powder X-ray diffraction pattern selected from those at about 14.27, about 17.97, about 18.66, about 21.42, about 22.25, about 25.67, and about 27.63 degrees 2-theta. In some embodiments, Form B of Compound 1 is characterized by two or more peaks in its powder X-ray diffraction pattern selected from those at about 14.27, about 17.97, about 18.66, about 21.42, about 22.25, about 25.67, and about 27.63 degrees 2-theta. In certain embodiments, Form B of Compound 1 is characterized by three or more peaks in its powder X-ray diffraction pattern selected from those at about 14.27, about 17.97, about 18.66, about 21.42, about 22.25, about 25.67, and about 27.63 degrees 2-theta. For example, in one embodiment, Form B of Compound 1 is characterized by a peak in its powder X-ray diffraction pattern at about 21.42. In another example, Form B of Compound 1 is characterized by peaks in its powder X-ray diffraction pattern at about 21.42 and one or more additional peaks selected from those at about 14.27, about 17.97, about 18.66, about 22.25, about 25.67, and about 27.63 degrees 2-theta. In another example, Form B of Compound 1 is characterized by peaks in its powder X-ray diffraction pattern at about 21.42 and two or more additional peaks selected from those at about 14.27, about 17.97, about 18.66, about 22.25, about 25.67, and about 27.63 degrees 2-theta. In another example, Form B of Compound 1 is characterized by peaks in its powder X-ray diffraction pattern at about 21.42 and three or more additional peaks selected from those at about 14.27, about 17.97, about 18.66, about 22.25, about 25.67, and about 27.63 degrees 2-theta. In another example, Form B of Compound 1 is characterized by peaks in its powder X-ray diffraction pattern at about 21.42 and four or more additional peaks selected from those at about 14.27, about 17.97, about 18.66, about 22.25, about 25.67, and about 27.63 degrees 2-theta. In another example, Form B of Compound 1 is characterized by peaks in its powder X-ray diffraction pattern at about 21.42 and about 14.27, and optionally one or more additional peaks selected from about 17.97, about 18.66, about 22.25, about 25.67, and about 27.63 degrees 2-theta. In another example, Form B of Compound 1 is characterized by peaks in its powder X-ray diffraction pattern at about 21.42, about 14.27, and about 17.97, and optionally one or more additional peaks selected from about 18.66, about 22.25, about 25.67, and about 27.63 degrees 2-theta. In another example, Form B of Compound 1 is characterized by peaks in its powder X-ray diffraction pattern at 21.42, about 14.27, about 17.97, about 25.67, and optionally one or more additional peaks selected from about 18.66, about 22.25, and about 27.63 degrees 2-theta. In another example, Form B of Compound 1 is characterized by peaks in its powder X-ray diffraction pattern at about 14.27, about 17.97, about 18.66, about 21.42, about 22.25, about 25.67, and about 27.63 degrees 2-theta. In another embodiment, Form B of Compound 1 is characterized by one or more peaks in its X-ray powder diffraction pattern selected from the group consisting of at about 11.24, 14.27, 17.97, 18.42, 18.66, 20.04, 21.42, 22.25, 23.39, 25.67, 26.41, and 27.63 degrees 2-theta. In particular embodiments, Form B of Compound 1 is characterized by all or substantially all of the peaks in its X-ray powder diffraction pattern selected from those at about 11.24, 14.27, 17.97, 18.42, 18.66, 20.04, 21.42, 22.25, 23.39, 25.67, 26.41, and 27.63 degrees 2-theta. In an exemplary embodiment, Form B of Compound 1 is characterized by all or substantially all of the peaks in its X-ray powder diffraction pattern selected from those at about:

| °2θ |
|---|
| 7.82 |
| 8.95 |
| 11.24 |
| 14.27 |
| 15.71 |
| 16.16 |
| 16.63 |
| 17.97 |
| 18.42 |
| 18.66 |
| 19.68 |
| 20.04 |
| 20.40 |
| 21.42 |
| 22.25 |
| 23.39 |
| 23.70 |
| 24.23 |
| 24.89 |
| 25.67 |
| 26.41 |
| 27.13 |
| 27.63 |
| 28.25 |
| 28.75 |
| 29.74 |
| 30.00 |

According to another embodiment, Form B of Compound 1 is characterized by one or more peaks in its powder X-ray diffraction pattern selected from those at about 14.3, about 18.0, about 18.7, about 21.4, about 22.3, about 25.7, and about 27.6 degrees 2-theta. In some embodiments, Form B of Compound 1 is characterized by two or more peaks in its powder X-ray diffraction pattern selected from those at about 14.3, about 18.0, about 18.7, about 21.4, about 22.3, about 25.7, and about 27.6 degrees 2-theta. In certain embodiments, Form B of Compound 1 is characterized by three or more peaks in its powder X-ray diffraction pattern selected from those at about 14.3, about 18.0, about 18.7, about 21.4, about 22.3, about 25.7, and about 27.6 degrees 2-theta. For example, in one embodiment, Form B of Compound 1 is characterized by a peak in its powder X-ray diffraction pattern at about 21.4. In another example, Form B of Compound 1 is characterized by peaks in its powder X-ray diffraction pattern at about 21.4 and one or more additional peaks selected from those at about 14.3, about 18.0, about 18.7, about 22.3, about 25.7, and about 27.6 degrees 2-theta. In another example, Form B of Compound 1 is characterized by peaks in its powder X-ray diffraction pattern at about 21.4 and two or more additional peaks selected from those at about 14.3, about 18.0, about 18.7, about 22.3, about 25.7, and about 27.6 degrees 2-theta. In another example, Form B of Compound 1 is characterized by peaks in its powder X-ray diffraction pattern at about 21.4 and three or more additional peaks selected from those at about 14.3, about 18.0, about 18.7, about 22.3, about 25.7, and about 27.6 degrees 2-theta. In another example, Form B of Compound 1 is characterized by peaks in its powder X-ray diffraction pattern at about 21.4 and four or more additional peaks selected from those at about 14.3, about 18.0, about 18.7, about 22.3, about 25.7, and about 27.6 degrees 2-theta. In another example, Form B of Compound 1 is characterized by peaks in its powder X-ray diffraction pattern at about 21.4 and about 14.3, and optionally one or more additional peaks selected from about 18.0, about 18.7, about 22.3, about 25.7, and about 27.6 degrees 2-theta. In another example, Form B of Compound 1 is characterized by peaks in its powder X-ray diffraction pattern at about 21.4, about 14.3, and about 18.0, and optionally one or more additional peaks selected from about 18.7, about 22.3, about 25.7, and about 27.6 degrees 2-theta. In another example, Form B of Compound 1 is characterized by peaks in its powder X-ray diffraction pattern at 21.4, about 14.3, about 18.0, about 25.7, and optionally one or more additional peaks selected from about 18.7, about 22.3, and about 27.6 degrees 2-theta. In another example, Form B of Compound 1 is characterized by peaks in its powder X-ray diffraction pattern at about 14.3, about 18.0, about 18.7, about 21.4, about 22.3, about 25.7, and about 27.6 degrees 2-theta. In another embodiment, Form B of Compound 1 is characterized by one or more peaks in its X-ray powder diffraction pattern selected from the group consisting of at about 11.2, 14.3, 18.0, 18.4, 18.7, 20.0, 21.4, 22.3, 23.4, 25.7, 26.4, and 27.6 degrees 2-theta. In particular embodiments, Form B of Compound 1 is characterized by substantially all of the peaks in its X-ray powder diffraction pattern selected from those at about 11.2, 14.3, 18.0, 18.4, 18.7, 20.0, 21.4, 22.3, 23.4, 25.7, 26.4, and 27.6 degrees 2-theta. In an exemplary embodiment, Form B of Compound 1 is characterized by substantially all of the peaks in its X-ray powder diffraction pattern selected from those at about:

| °2θ |
|---|
| 7.8 |
| 9.0 |
| 11.2 |
| 14.3 |
| 15.7 |

| °2θ |
|---|
| 16.2 |
| 16.6 |
| 18.0 |
| 18.4 |
| 18.7 |
| 19.7 |
| 20.0 |
| 20.4 |
| 21.4 |
| 22.3 |
| 23.4 |
| 23.7 |
| 24.2 |
| 24.9 |
| 25.7 |
| 26.4 |
| 27.1 |
| 27.6 |
| 28.3 |
| 28.8 |
| 29.7 |
| 30.0 |

Figure 5:
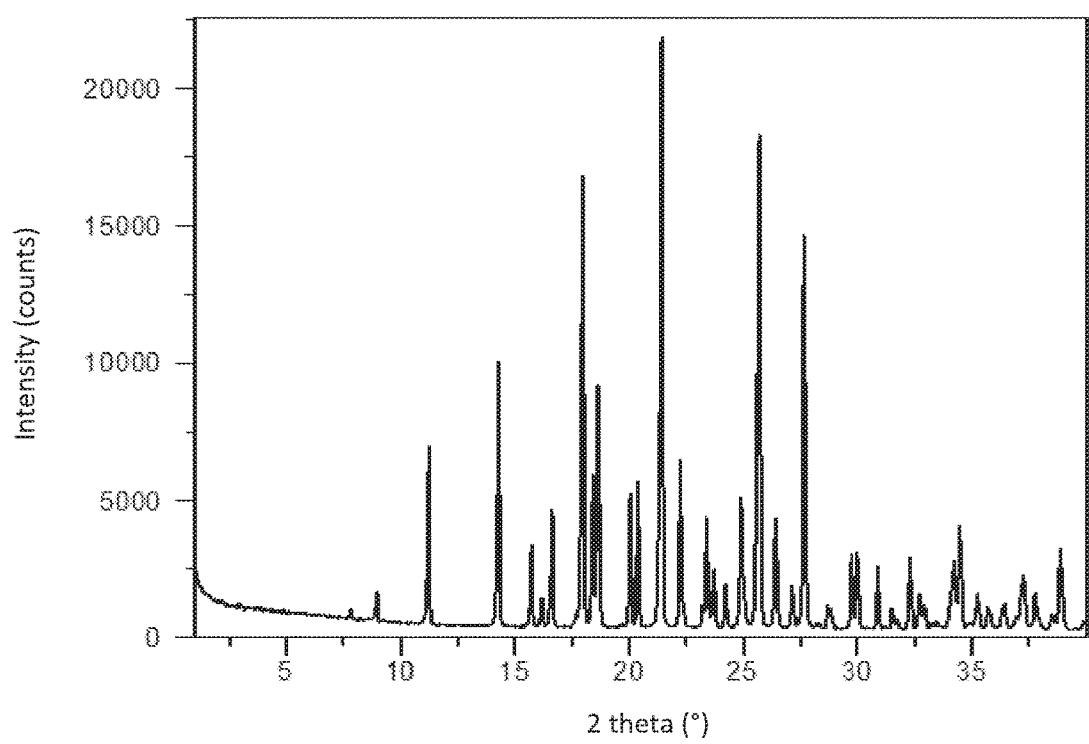
FIG. 5 depicts the XRPD pattern for Form B of Compound 1.
Figure 6:
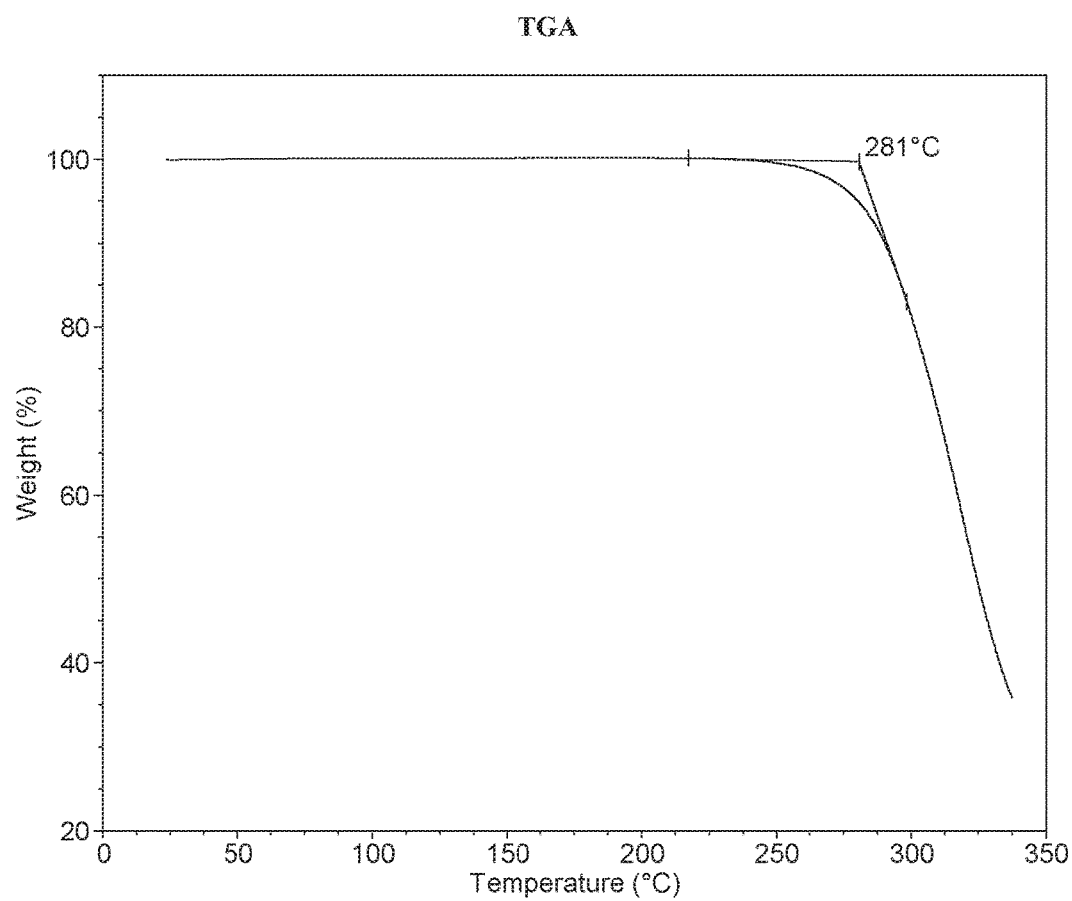
FIG. 6 depicts the TGA pattern for Form B of Compound 1.
Figure 7:
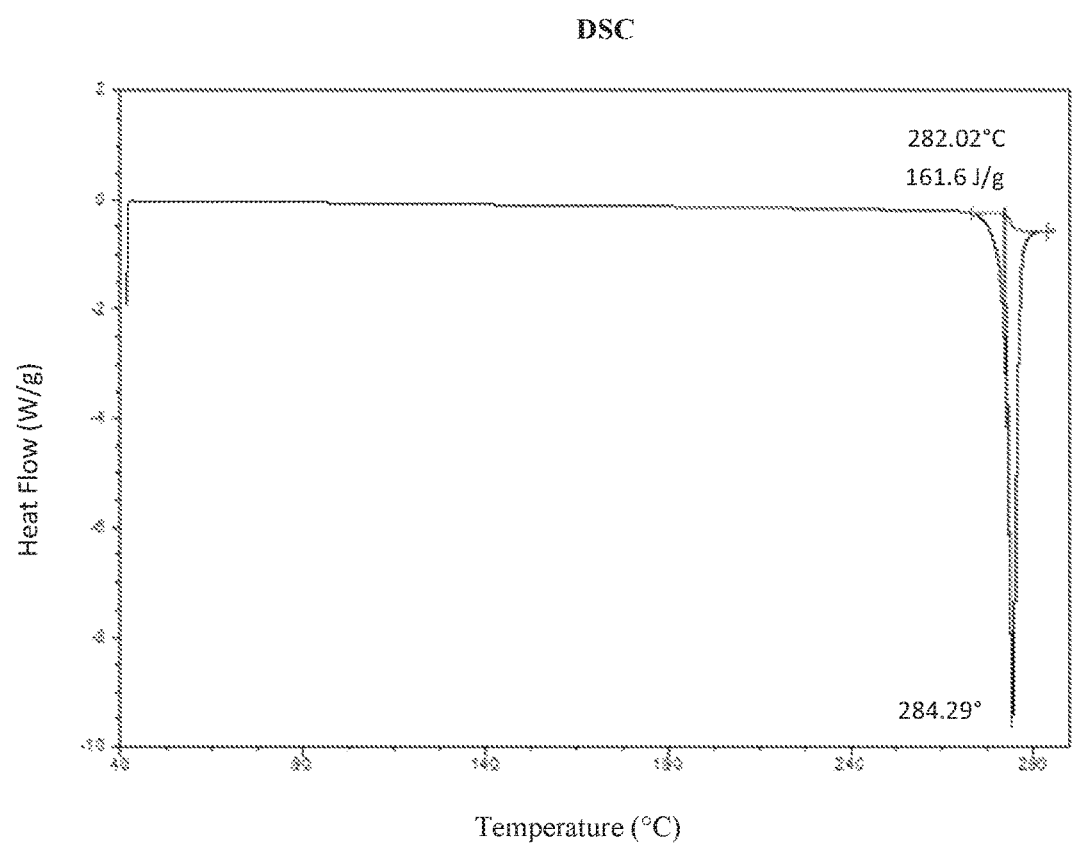
FIG. 7 depicts the DSC pattern for Form B of Compound 1.
Figure 8:
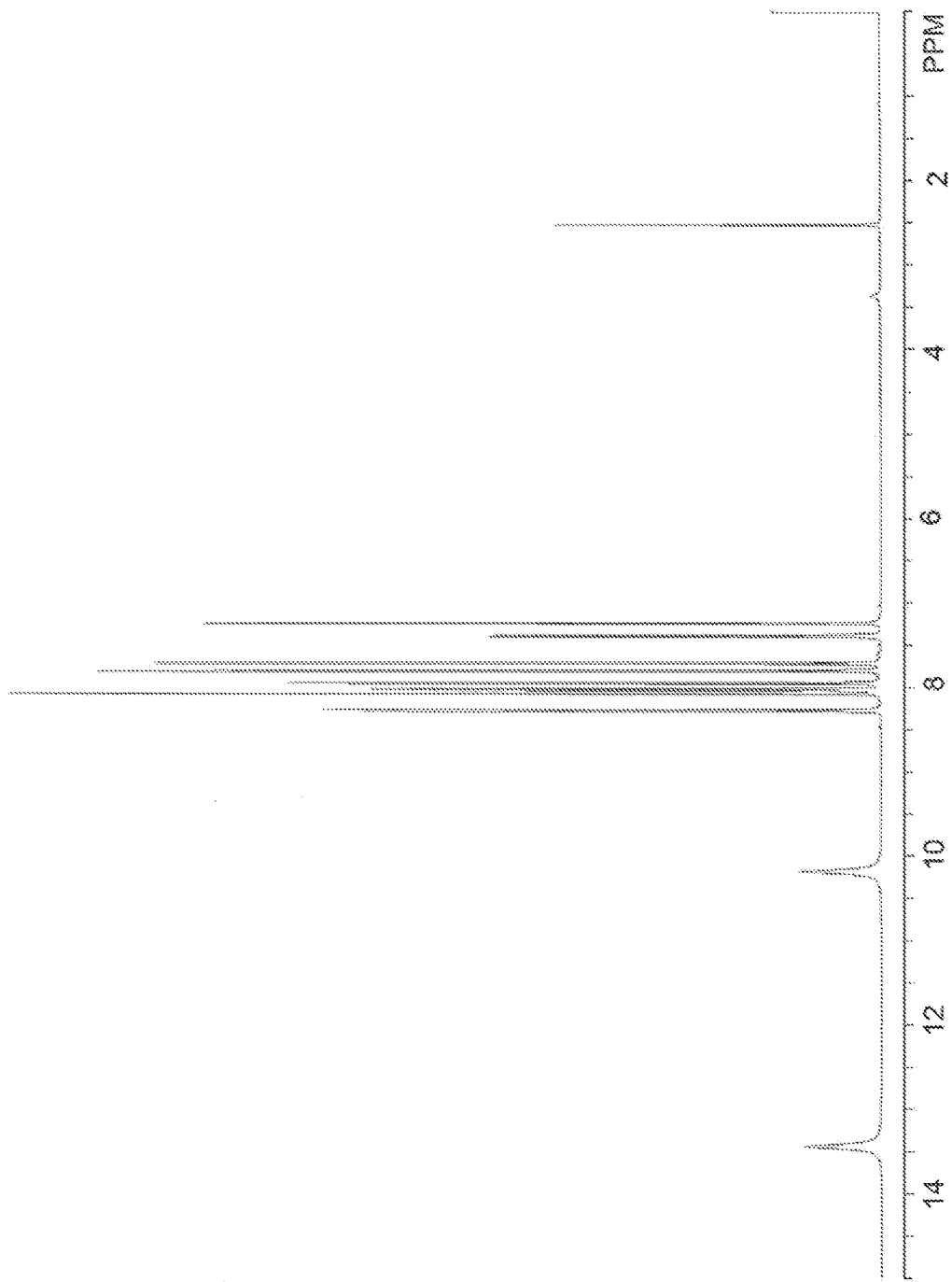
FIG. 8 depicts the $^1$H NMR spectrum for Form B of Compound 1.

According to one aspect, Form B of Compound 1 has a powder X-ray diffraction pattern substantially similar to that depicted in FIG. 5. According to another aspect, Form B of Compound 1 has a thermogravimetric analysis pattern substantially similar to that depicted in FIG. 6. Accordingly to yet another aspect, Form B of Compound 1 has a differential scanning calorimetry pattern substantially similar to that depicted in FIG. 7. According to a further embodiment, Form B of Compound 1 has a $^1$H NMR spectrum substantially similar to that depicted in FIG. 8. Form B of Compound 1 can be characterized by substantial similarity to two or more of these figures simultaneously.

In certain embodiments, Compound 1 is an isopropyl alcohol (IPA) solvate crystal form. In some embodiments, the present invention provides an IPA solvate polymorphic form of Compound 1 referred to herein as Form C, wherein there is about 0.5 mol of IPA per mol of Compound 1. Form C of Compound 1 is also known as Form VI of Compound 1.

In certain embodiments, the present invention provides Form C of Compound 1. According to one embodiment, Form C of Compound 1 is characterized by one or more peaks in its powder X-ray diffraction pattern selected from those at about 8.11, about 11.43, about 17.73, about 18.92, about 19.42, about 20.54, and about 25.24 degrees 2-theta. In some embodiments, Form C of Compound 1 is characterized by two or more peaks in its powder X-ray diffraction pattern selected from those at about 8.11, about 11.43, about 17.73, about 18.92, about 19.42, about 20.54, and about 25.24 degrees 2-theta. In certain embodiments, Form C of Compound 1 is characterized by three or more peaks in its powder X-ray diffraction pattern selected from those at about 8.11, about 11.43, about 17.73, about 18.92, about 19.42, about 20.54, and about 25.24 degrees 2-theta. For example, in one embodiment, Form C of Compound 1 is characterized by a peak in its powder X-ray diffraction pattern at about 19.42. In another example, Form C of Compound 1 is characterized by peaks in its powder X-ray diffraction pattern at about 19.42 and one or more additional peaks selected from those at about 8.11, about 11.43, about 17.73, about 18.92, about 20.54, and about 25.24 degrees 2-theta. In another example, Form C of Compound 1 is characterized by peaks in its powder X-ray diffraction pattern at about 19.42 and two or more additional peaks selected from those at about 8.11, about 11.43, about 17.73, about 18.92, about 20.54, and about 25.24 degrees 2-theta. In another example, Form C of Compound 1 is characterized by peaks in its powder X-ray diffraction pattern at about 19.42 and three or more additional peaks selected from those at about 8.11, about 11.43, about 17.73, about 18.92, about 20.54, and about 25.24 degrees 2-theta. In another example, Form C of Compound 1 is characterized by peaks in its powder X-ray diffraction pattern at about 19.42 and four or more additional peaks selected from those at about 8.11, about 11.43, about 17.73, about 18.92, about 20.54, and about 25.24 degrees 2-theta. In another embodiment, Form C of Compound 1 is characterized by one or more peaks in its X-ray powder diffraction pattern selected from the group consisting of at about 8.11, 8.93, 10.16, 11.43, 15.18, 16.28, 17.73, 18.92, 19.42, 20.54, 22.60, 23.03, 23.84, 25.24, and 26.16 degrees 2-theta. In particular embodiments, Form C of Compound 1 is characterized by all or substantially all of the peaks in its X-ray powder diffraction pattern selected from those at about 8.11, 8.93, 10.16, 11.43, 15.18, 16.28, 17.73, 18.92, 19.42, 20.54, 22.60, 23.03, 23.84, 25.24, and 26.16 degrees 2-theta. In an exemplary embodiment, Form C of compound 1 is characterized by all or substantially all of the peaks in its X-ray powder diffraction pattern selected from those at about:

| °2θ |
|---|
| 8.11 |
| 8.93 |
| 10.16 |
| 10.75 |
| 11.43 |
| 12.70 |
| 13.05 |
| 14.11 |
| 14.76 |
| 15.18 |
| 15.64 |
| 16.28 |
| 17.73 |
| 17.93 |
| 18.22 |
| 18.40 |
| 18.92 |
| 19.42 |
| 19.89 |
| 20.54 |
| 20.93 |
| 21.33 |
| 21.77 |
| 22.60 |
| 23.03 |
| 23.84 |
| 24.68 |
| 25.24 |
| 26.16 |
| 26.53 |
| 27.06 |
| 27.46 |
| 27.73 |
| 28.15 |
| 29.21 |
| 29.62 |
| 29.78 |

In certain embodiments, the present invention provides Form C of Compound 1. According one embodiment, Form C of Compound 1 is characterized by one or more peaks in its powder X-ray diffraction pattern selected from those at about 8.1, about 11.4, about 17.7, about 18.9, about 19.4, about 20.5, and about 25.2 degrees 2-theta. In some embodiments, Form C of Compound 1 is characterized by two or more peaks in its powder X-ray diffraction pattern selected from those at about 8.1, about 11.4, about 17.7, about 18.9, about 19.4, about 20.5, and about 25.2 degrees 2-theta. In certain embodiments, Form C of Compound 1 is characterized by three or more peaks in its powder X-ray diffraction pattern selected from those at about 8.1, about 11.4, about 17.7, about 18.9, about 19.4, about 20.5, and about 25.2 degrees 2-theta. For example, in one embodiment, Form C of Compound 1 is characterized by a peak in its powder X-ray diffraction pattern at about 19.4. In another example, Form C of Compound 1 is characterized by peaks in its powder X-ray diffraction pattern at about 19.4 and one or more additional peaks selected from those at about 8.1, about 11.4, about 17.7, about 18.9, about 20.5, and about 25.2 degrees 2-theta. In another example, Form C of Compound 1 is characterized by peaks in its powder X-ray diffraction pattern at about 19.4 and two or more additional peaks selected from those at about 8.1, about 11.4, about 17.7, about 18.9, about 20.5, and about 25.2 degrees 2-theta. In another example, Form C of Compound 1 is characterized by peaks in its powder X-ray diffraction pattern at about 19.4 and three or more additional peaks selected from those at about 8.1, about 11.4, about 17.7, about 18.9, about 20.5, and about 25.2 degrees 2-theta. In another example, Form C of Compound 1 is characterized by peaks in its powder X-ray diffraction pattern at about 19.4 and four or more additional peaks selected from those at about 8.1, about 11.4, about 17.7, about 18.9, about 20.5, and about 25.2 degrees 2-theta. In another embodiment, Form C of Compound 1 is characterized by one or more peaks in its X-ray powder diffraction pattern selected from the group consisting of at about 8.1, 8.9, 10.2, 11.4, 15.2, 16.3, 17.7, 18.9, 19.4, 20.5, 22.6, 23.0, 23.8, 25.2, and 26.2 degrees 2-theta. In particular embodiments, Form C of Compound 1 is characterized by all or substantially all of the peaks in its X-ray powder diffraction pattern selected from those at about 8.1, 8.9, 10.2, 11.4, 15.2, 16.3, 17.7, 18.9, 19.4, 20.5, 22.6, 23.0, 23.8, 25.2, and 26.2 degrees 2-theta. In an exemplary embodiment, Form C of compound 1 is characterized by all or substantially all of the peaks in its X-ray powder diffraction pattern selected from those at about:

| °2θ |
|---|
| 8.1 |
| 8.9 |
| 10.2 |
| 10.8 |
| 11.4 |
| 12.7 |
| 13.1 |
| 14.1 |
| 14.8 |
| 15.2 |
| 15.6 |
| 16.3 |
| 17.7 |
| 17.9 |
| 18.2 |
| 18.4 |
| 18.9 |
| 19.4 |
| 19.9 |
| 20.5 |
| 20.9 |
| 21.3 |
| 21.8 |
| 22.6 |
| 23.0 |
| 23.8 |

-continued

| °2θ |
|---|
| 24.7 |
| 25.2 |
| 26.2 |
| 26.5 |
| 27.1 |
| 27.5 |
| 27.7 |
| 28.2 |
| 29.2 |
| 29.6 |
| 29.8 |

Figure 9:
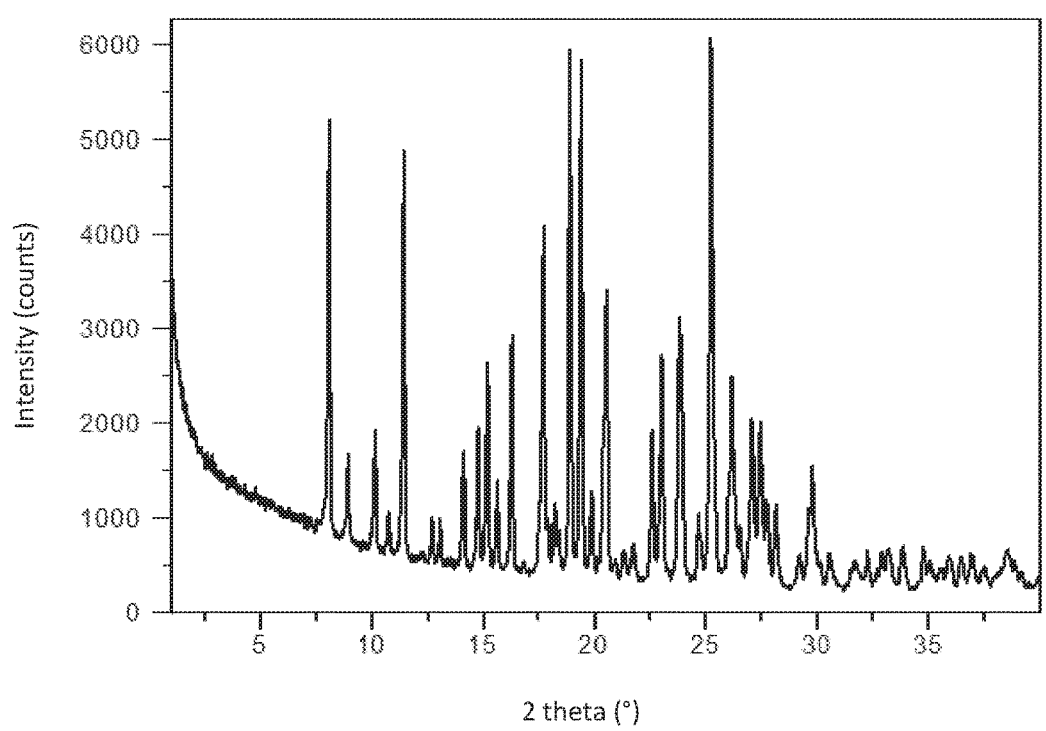
FIG. 9 depicts the XRPD pattern for Form C of Compound 1.
Figure 10:
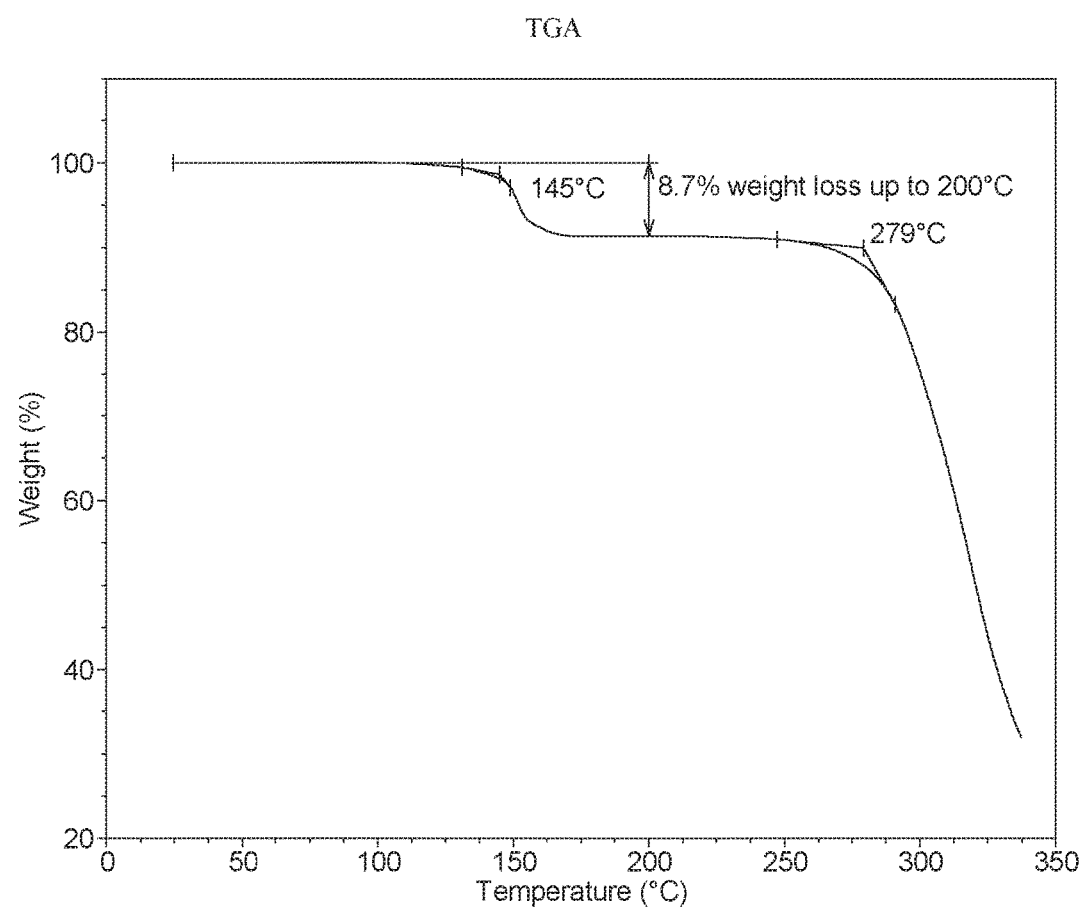
FIG. 10 depicts the TGA pattern for Form C of Compound 1.
Figure 11:
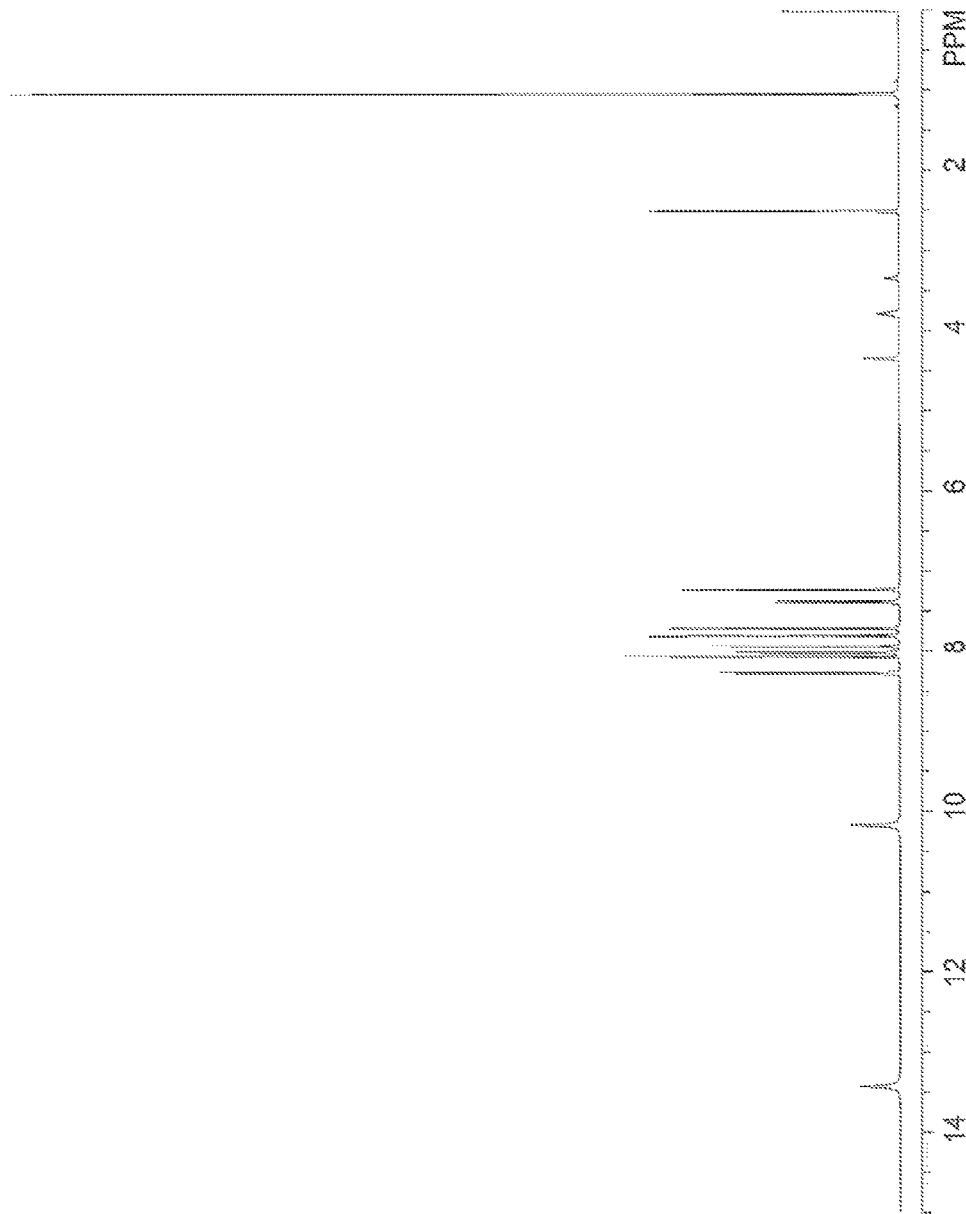
FIG. 11 depicts the $^1$H NMR spectrum for Form C of Compound 1.

According to one aspect, Form C of Compound 1 has a powder X-ray diffraction pattern substantially similar to that depicted in FIG. 9. According to another aspect, Form C of Compound 1 has a thermogravimetric analysis pattern substantially similar to that depicted in FIG. 10. According to a further embodiment, Form C of Compound 1 has a $^1$H NMR spectrum substantially similar to that depicted in FIG. 11. Form C of Compound 1 can be characterized by substantial similarity to two or more of these figures simultaneously.

In certain embodiments, the present invention provides Form D of Compound 1. Form D of Compound 1 is also known as Form IX of Compound 1.

According to one embodiment, Form D of Compound 1 is characterized by one or more peaks in its powder X-ray diffraction pattern selected from those at about 5.50, about 9.38, about 22.50, about 23.75, about 24.96, about 27.23, and about 27.34 degrees 2-theta. In some embodiments, Form D of Compound 1 is characterized by two or more peaks in its powder X-ray diffraction pattern selected from those at about 5.50, about 9.38, about 22.50, about 23.75, about 24.96, about 27.23, and about 27.34 degrees 2-theta. In certain embodiments, Form D of Compound 1 is characterized by three or more peaks in its powder X-ray diffraction pattern selected from those at about 5.50, about 9.38, about 22.50, about 23.75, about 24.96, about 27.23, and about 27.34 degrees 2-theta. For example, in one embodiment, Form D of Compound 1 is characterized by a peak in its powder X-ray diffraction pattern at about 5.50. In another example, Form D of Compound 1 is characterized by peaks in its powder X-ray diffraction pattern at about 5.50 and one or more additional peaks selected from those at about 9.38, about 22.50, about 23.75, about 24.96, about 27.23, and about 27.34 degrees 2-theta. In another example, Form D of Compound 1 is characterized by peaks in its powder X-ray diffraction pattern at about 5.50 and two or more additional peaks selected from those at about 9.38, about 22.50, about 23.75, about 24.96, about 27.23, and about 27.34 degrees 2-theta. In another example, Form D of Compound 1 is characterized by peaks in its powder X-ray diffraction pattern at about 5.50 and three or more additional peaks selected from those at about 9.38, about 22.50, about 23.75, about 24.96, about 27.23, and about 27.34 degrees 2-theta. In another example, Form D of Compound 1 is characterized by peaks in its powder X-ray diffraction pattern at about 5.50 and four or more additional peaks selected from those at about 9.38, about 22.50, about 23.75, about 24.96, about 27.23, and about 27.34 degrees 2-theta. In one embodiment, Form D of Compound 1 is characterized by one or more peaks in its X-ray powder diffraction pattern selected from the group consisting of at about 5.50, 9.38, 15.23, 15.48, 22.50, 23.75, 24.96, 27.23, 27.34, 27.83, 28.78, and 29.26 degrees 2-theta. In particular embodiments, Form D of Compound 1 is characterized by all or substantially all of the peaks in its X-ray powder diffraction pattern selected from those at about 5.50, 9.38, 15.23, 15.48, 22.50, 23.75, 24.96, 27.23, 27.34, 27.83, 28.78, and 29.26 degrees 2-theta. In an exemplary embodiment, Form D of Compound 1 is characterized by all or substantially all of the peaks in its X-ray powder diffraction pattern selected from those at about:

| °2θ |
|---|
| 5.50 |
| 8.07 |
| 9.38 |
| 11.02 |
| 13.39 |
| 15.23 |
| 15.48 |
| 16.21 |
| 16.58 |
| 18.25 |
| 18.85 |
| 20.61 |
| 22.17 |
| 22.50 |
| 23.10 |
| 23.75 |
| 24.42 |
| 24.96 |
| 26.16 |
| 26.36 |
| 27.23 |
| 27.34 |
| 27.83 |
| 28.34 |
| 28.78 |
| 29.26 |
| 30.20 |

According to one embodiment, Form D of Compound 1 is characterized by one or more peaks in its powder X-ray diffraction pattern selected from those at about 5.5, about 9.4, about 22.5, about 23.8, about 25.0, about 27.2, and about 27.3 degrees 2-theta. In some embodiments, Form D of Compound 1 is characterized by two or more peaks in its powder X-ray diffraction pattern selected from those at about 5.5, about 9.4, about 22.5, about 23.8, about 25.0, about 27.2, and about 27.3 degrees 2-theta. In certain embodiments, Form D of Compound 1 is characterized by three or more peaks in its powder X-ray diffraction pattern selected from those at about 5.5, about 9.4, about 22.50 about 23.8, about 25.0, about 27.2, and about 27.3 degrees 2-theta. For example, in one embodiment, Form D of Compound 1 is characterized by a peak in its powder X-ray diffraction pattern at about 5.5. In another example, Form D of Compound 1 is characterized by peaks in its powder X-ray diffraction pattern at about 5.5 and one or more additional peaks selected from those at about 9.4, about 22.5, about 23.8, about 25.0, about 27.2, and about 27.3 degrees 2-theta. In another example, Form D of Compound 1 is characterized by peaks in its powder X-ray diffraction pattern at about 5.5 and two or more additional peaks selected from those at about 9.4, about 22.5, about 23.8, about 25.0, about 27.2, and about 27.3 degrees 2-theta. In another example, Form D of Compound 1 is characterized by peaks in its powder X-ray diffraction pattern at about 5.5 and three or more additional peaks selected from those at about 9.4, about 22.5, about 23.8, about 25.0, about 27.2, and about 27.3 degrees 2-theta. In another example, Form D of Compound 1 is characterized by peaks in its powder X-ray diffraction pattern at about 5.5 and four or more additional peaks selected from those at about 9.4, about 22.5, about 23.8, about 25.0, about 27.2, and about 27.3 degrees 2-theta. In one embodiment, Form D of Compound 1 is characterized by one or more peaks in its X-ray powder diffraction pattern selected from the group consisting of at about 5.5, 9.4, 15.2, 15.5, 22.5, 23.8, 25.0, 27.2, 27.3, 27.8, 28.8, and 29.3 degrees 2-theta. In particular embodiments, Form D of Compound 1 is characterized by all or substantially all of the peaks in its X-ray powder diffraction pattern selected from those at about 5.5, 9.4, 15.2, 15.5, 22.5, 23.8, 25.0, 27.2, 27.3, 27.8, 28.8, and 29.3 degrees 2-theta. In an exemplary embodiment, Form D of Compound 1 is characterized by all or substantially all of the peaks in its X-ray powder diffraction pattern selected from those at about:

| °2θ |
|---|
| 5.5 |
| 8.1 |
| 9.4 |
| 11.0 |
| 13.3 |
| 15.2 |
| 15.5 |
| 16.2 |
| 16.6 |
| 18.3 |
| 18.9 |
| 20.6 |
| 22.2 |
| 22.5 |
| 23.1 |
| 23.8 |
| 24.4 |
| 25.0 |
| 26.2 |
| 26.4 |
| 27.2 |
| 27.3 |
| 27.8 |
| 28.3 |
| 28.8 |
| 29.3 |
| 30.2 |

Figure 12:
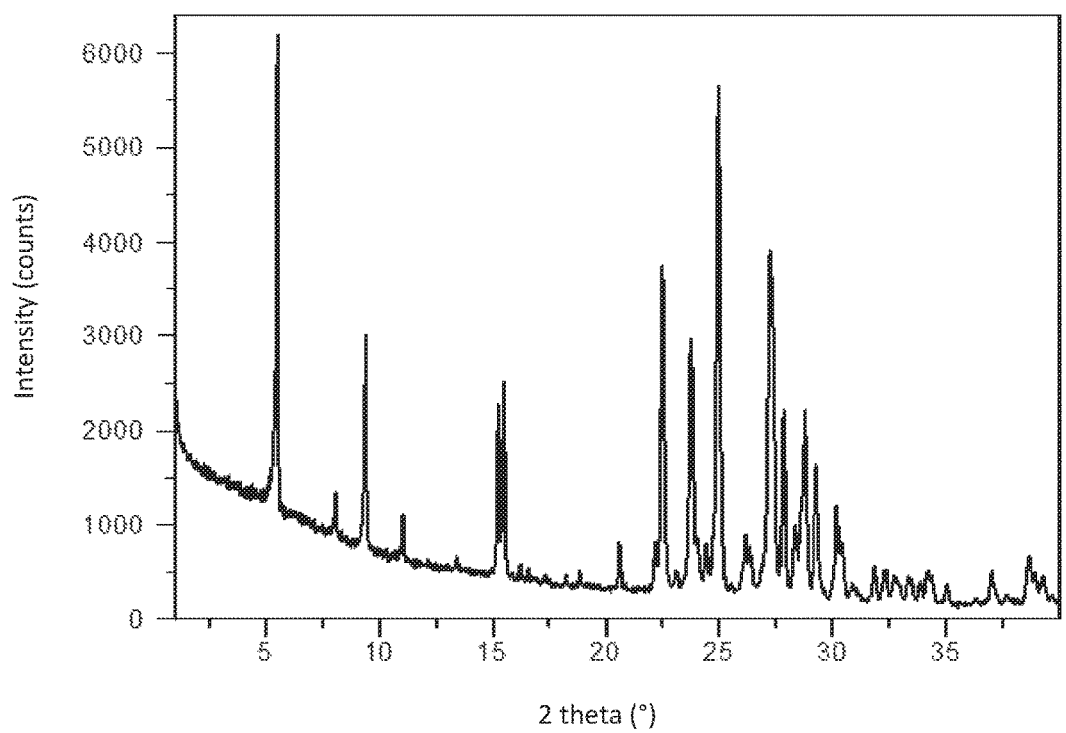
FIG. 12 depicts the XRPD pattern for Form D of Compound 1.
Figure 13:
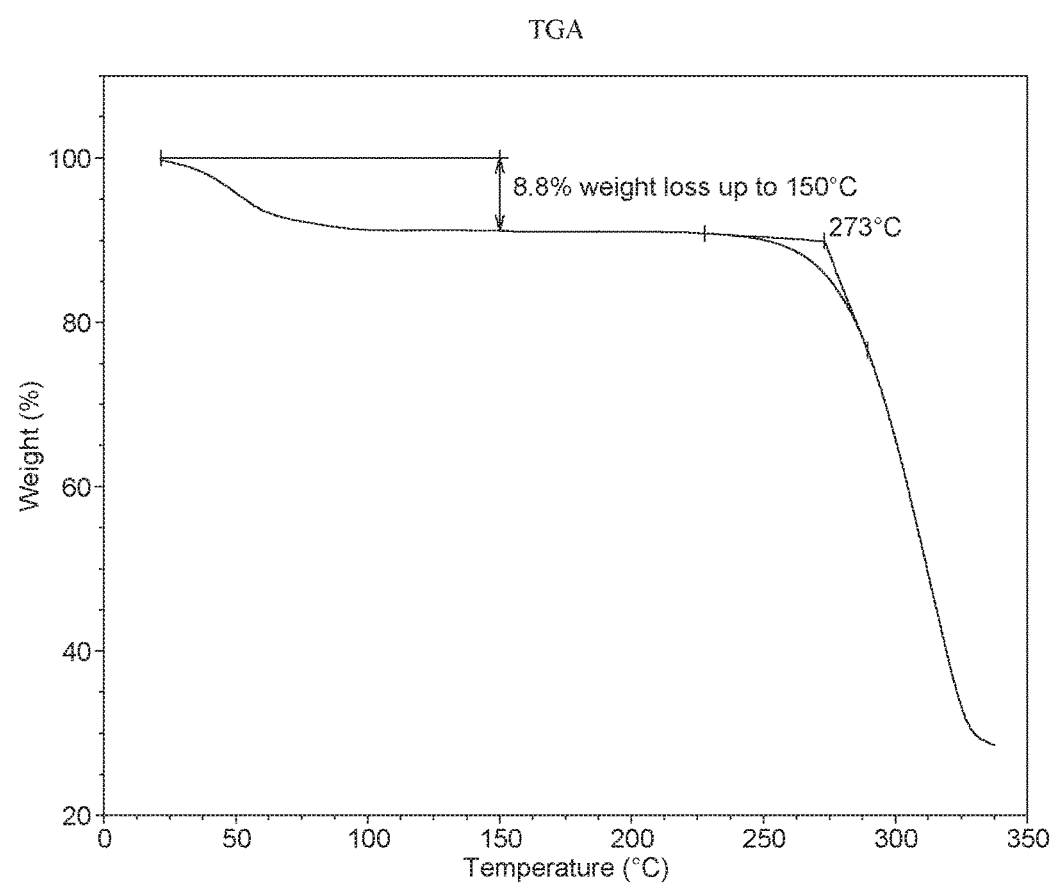
FIG. 13 depicts TGA pattern for Form D of Compound 1.
Figure 14:
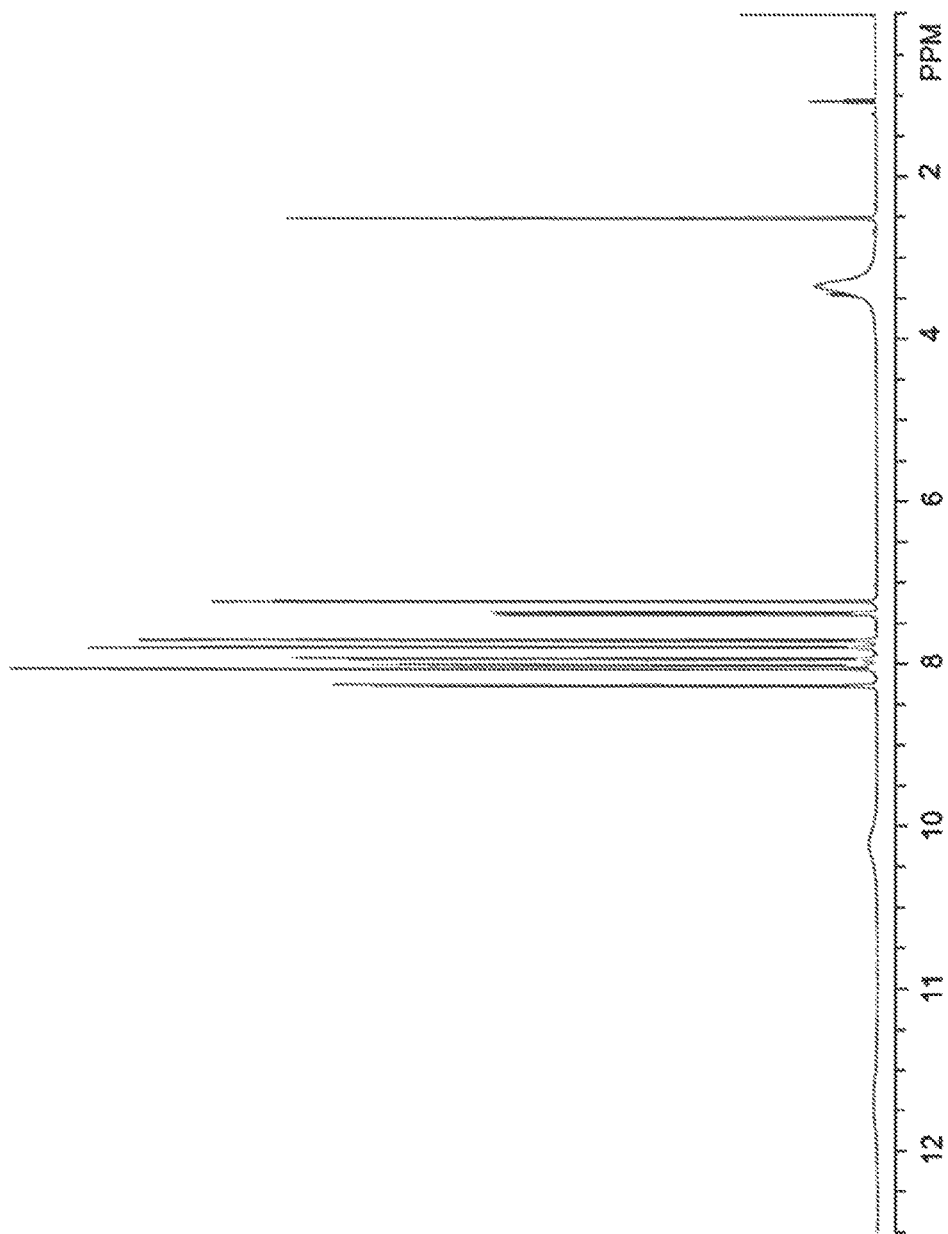
FIG. 14 depicts the $^1$H NMR spectrum for Form D of Compound 1.

According to one aspect, Form D of Compound 1 has a powder X-ray diffraction pattern substantially similar to that depicted in FIG. 12. According to another aspect, Form D of Compound 1 has a thermogravimetric analysis pattern substantially similar to that depicted in FIG. 13. According to a further embodiment, Form D of Compound 1 has a $^1$H NMR spectrum substantially similar to that depicted in FIG. 14. Form D of Compound 1 can be characterized by substantial similarity to two or more of these figures simultaneously.

It will be appreciated that any of the above-described polymorph forms can be characterized, for example, by reference to any of the peaks in their respective X-ray diffraction patterns. Accordingly, in some embodiments, a polymorph described herein is characterized by one, two, three, four, five, six, seven, eight, nine, ten, eleven, twelve, thirteen, fourteen, fifteen, sixteen, seventeen, eighteen, nineteen, twenty or more XRPD peaks (° 2θ). According to another embodiment, the present invention provides compound 1 as an amorphous solid. Amorphous solids are well known to one of ordinary skill in the art and are typically prepared by such methods as lyophilization, melting, and precipitation from supercritical fluid, among others.

General Methods of Providing Compound 1:

Compound 1 is prepared according to the methods described in detail in the '181 application, the entirety of which is hereby incorporated herein by reference. The various solid forms of Compound 1 can be prepared by dissolving compound 1 in various suitable solvents and then causing Compound 1 to return to the solid phase. Specific combinations of solvents and conditions under which Compound 1 return to the solid phase are discussed in greater detail in the Examples.

A suitable solvent may solubilize Compound 1, either partially or completely. Examples of suitable solvents useful in the present invention are a protic solvent, a polar aprotic solvent, or mixtures thereof. In certain embodiments, suitable solvents include an ether, an ester, an alcohol, a ketone, or a mixture thereof. In certain embodiments, the suitable solvent is methanol, ethanol, isopropanol, or acetone wherein said solvent is anhydrous or in combination with water, methyl tert-butyl ether (MTBE) or heptane. In other embodiments, suitable solvents include tetrahydrofuran, 1,4-dioxane, dimethylformamide, dimethylsulfoxide, glyme, diglyme, methyl ethyl ketone, N-methyl-2-pyrrolidone, methyl t-butyl ether, t-butanol, n-butanol, and acetonitrile.

According to another embodiment, the present invention provides a method for preparing a solid form of Compound 1, comprising the steps of dissolving Compound 1 with a suitable solvent and optionally heating to form a solution thereof; and isolating Compound 1.

As described generally above, Compound 1 is dissolved in a suitable solvent, optionally with heating. In certain embodiments Compound 1 is dissolved at about 50 to about 60° C. In still other embodiments, Compound 1 is dissolved at the boiling temperature of the solvent. In other embodiments, Compound 1 is dissolved without heating (e.g., at ambient temperature, approximately 20-25° C.).

In certain embodiments, Compound 1 precipitates from the mixture. In another embodiment, Compound 1 crystallizes from the mixture. In other embodiments, Compound 1 crystallizes from solution following seeding of the solution (i.e., adding crystals of Compound 1 to the solution).

Crystalline Compound 1 can precipitate out of the reaction mixture, or be generated by removal of part or all of the solvent through methods such as evaporation, distillation, filtration (e.g., nanofiltration, ultrafiltration), reverse osmosis, absorption and reaction, by adding an anti-solvent (e.g., water, MTBE and/or heptane), by cooling (e.g., crash cooling) or by different combinations of these methods.

According to another embodiment, the present invention provides a method for preparing a solid form of Compound 1, comprising the step of slurrying Compound 1 with a suitable solvent.

As described generally above, Compound 1 is optionally isolated. It will be appreciated that Compound 1 may be isolated by any suitable physical means known to one of ordinary skill in the art. In certain embodiments, precipitated solid Compound 1 is separated from the supernatant by filtration. In other embodiments, precipitated solid Compound 1 is separated from the supernatant by decanting the supernatant.

In certain embodiments, precipitated solid Compound 1 is separated from the supernatant by filtration.

In certain embodiments, isolated Compound 1 is dried in air. In other embodiments isolated Compound 1 is dried under reduced pressure, optionally at elevated temperature.

Uses, Formulation and Administration
Pharmaceutically Acceptable Compositions

According to another embodiment, the invention provides a composition comprising Compound 1 and a pharmaceutically acceptable carrier, adjuvant, or vehicle. The amount of Compound 1 in compositions of this invention is such that it is effective to inhibit s-nitrosoglutathione reductase in a biological sample or in a patient. In certain embodiments, a composition of this invention is formulated for administration to a patient in need of such composition. In some embodiments, a composition of this invention is formulated for oral administration to a patient.

The term "patient", as used herein, means an animal, preferably a mammal, and most preferably a human.

The term "pharmaceutically acceptable carrier, adjuvant, or vehicle" refers to a non-toxic carrier, adjuvant, or vehicle that does not destroy the pharmacological activity of the compound with which it is formulated. Pharmaceutically acceptable carriers, adjuvants or vehicles that may be used in the compositions of this invention include, but are not limited to, ion exchangers, alumina, aluminum stearate, lecithin, serum proteins, such as human serum albumin, buffer substances such as phosphates, glycine, sorbic acid, potassium sorbate, partial glyceride mixtures of saturated vegetable fatty acids, water, salts or electrolytes, such as protamine sulfate, disodium hydrogen phosphate, potassium hydrogen phosphate, sodium chloride, zinc salts, colloidal silica, magnesium trisilicate, polyvinyl pyrrolidone, cellulose-based substances, polyethylene glycol, Vitamin E polyethylene glycol succinate (d-alpha tocopheryl polyethylene glycol 1000 succinate), sodium carboxymethylcellulose, polyacrylates, waxes, polyethylene-polyoxypropylene-block polymers, and wool fat.

Compositions of the present invention may be administered orally, parenterally, by inhalation spray, topically, rectally, nasally, buccally, vaginally or via an implanted reservoir. The term "parenteral" as used herein includes subcutaneous, intravenous, intramuscular, intra-articular, intra-synovial, intrasternal, intrathecal, intrahepatic, intralesional and intracranial injection or infusion techniques. Preferably, the compositions are administered orally, intraperitoneally or intravenously. Sterile injectable forms of the compositions of this invention may be an aqueous or oleaginous suspension. These suspensions may be formulated according to techniques known in the art using suitable dispersing or wetting agents and suspending agents. The sterile injectable preparation may also be a sterile injectable solution or suspension in a non-toxic parenterally acceptable diluent or solvent, for example as a solution in 1,3-butanediol. Among the acceptable vehicles and solvents that may be employed are water, Ringer's solution and isotonic sodium chloride solution. In addition, sterile, fixed oils are conventionally employed as a solvent or suspending medium.

For this purpose, any bland fixed oil may be employed including synthetic mono- or di-glycerides. Fatty acids, such as oleic acid and its glyceride derivatives are useful in the preparation of injectables, as are natural pharmaceutically-acceptable oils, such as olive oil or castor oil, especially in their polyoxyethylated versions. These oil solutions or suspensions may also contain a long-chain alcohol diluent or dispersant, such as carboxymethyl cellulose or similar dispersing agents that are commonly used in the formulation of pharmaceutically acceptable dosage forms including emulsions and suspensions. Other commonly used surfactants, such as Tweens, Spans and other emulsifying agents or bioavailability enhancers which are commonly used in the manufacture of pharmaceutically acceptable solid, liquid, or other dosage forms may also be used for the purposes of formulation.

Pharmaceutically acceptable compositions of this invention may be orally administered in any orally acceptable dosage form including, but not limited to, capsules, tablets, aqueous and non-aqueous suspensions or solutions. In the case of tablets for oral use, carriers commonly used include lactose and corn starch. Lubricating agents, such as magnesium stearate, are also typically added. For oral administration in a capsule form, useful diluents include lactose and dried cornstarch. When aqueous suspensions are required for oral use, the active ingredient is typically combined with emulsifying and suspending agents. If desired, certain sweetening, flavoring or coloring agents may also be added.

Alternatively, pharmaceutically acceptable compositions of this invention may be administered in the form of suppositories for rectal administration. These can be prepared by mixing the agent with a suitable non-irritating excipient that is solid at room temperature but liquid at rectal temperature and therefore will melt in the rectum to release the drug. Such materials include cocoa butter, beeswax and polyethylene glycols.

Pharmaceutically acceptable compositions of this invention may also be administered topically, especially when the target of treatment includes areas or organs readily accessible by topical application, including diseases of the eye, the skin, or the lower intestinal tract. Suitable topical formulations are readily prepared for each of these areas or organs.

Topical application for the lower intestinal tract can be effected in a rectal suppository formulation (see above) or in a suitable enema formulation. Topically-transdermal patches may also be used.

For topical applications, provided pharmaceutically acceptable compositions may be formulated in a suitable ointment containing the active component suspended or dissolved in one or more carriers. Carriers for topical administration of Compound 1 include, but are not limited to, mineral oil, liquid petrolatum, white petrolatum, propylene glycol, polyoxyethylene, polyoxypropylene compound, emulsifying wax and water. Alternatively, provided pharmaceutically acceptable compositions can be formulated in a suitable lotion or cream containing the active components suspended or dissolved in one or more pharmaceutically acceptable carriers. Suitable carriers include, but are not limited to, mineral oil, sorbitan monostearate, polysorbate 60, cetyl esters wax, cetearyl alcohol, 2-octyldodecanol, benzyl alcohol and water.

For ophthalmic use, provided pharmaceutically acceptable compositions may be formulated as micronized suspensions in isotonic, pH adjusted sterile saline, or, preferably, as solutions in isotonic, pH adjusted sterile saline, either with or without a preservative such as benzylalkonium chloride. Alternatively, for ophthalmic uses, the pharmaceutically acceptable compositions may be formulated in an ointment such as petrolatum.

Pharmaceutically acceptable compositions of this invention may also be administered by nasal aerosol or inhalation. Such compositions are prepared according to techniques well-known in the art of pharmaceutical formulation and may be prepared as solutions in saline, employing benzyl alcohol or other suitable preservatives, absorption promoters to enhance bioavailability, fluorocarbons, and/or other conventional solubilizing or dispersing agents.

In some embodiments, pharmaceutically acceptable compositions of this invention are formulated for oral administration.

The amount of Compound 1 that may be combined with the carrier materials to produce a composition in a single dosage form will vary depending upon the host treated, the particular mode of administration. In certain embodiments, provided compositions are formulated so that a dosage of between 0.01-100 mg/kg body weight/day of Compound 1 can be administered to a patient receiving these compositions.

It should also be understood that a specific dosage and treatment regimen for any particular patient will depend upon a variety of factors, including the activity of the specific compound employed, the age, body weight, general health, sex, diet, time of administration, rate of excretion, drug combination, and the judgment of the treating physician and the severity of the particular disease being treated.

Uses of Compounds and Pharmaceutically Acceptable Compositions

Compound 1 and compositions described herein are generally useful for the treatment of diseases wherein there is a need for increased NO bioactivity. Compound 1 is active in a variety of assays and therapeutic models demonstrating selective and reversible inhibition of s-nitrosoglutathione reductase. Notably, Compound 1 demonstrates efficacy in asthma, COPD, cystic fibrosis, and IBD models (disclosed in the '181 application, U.S. application 62/061,557; U.S. application 62/093,712; U.S. application 62/138,792; and U.S. application 62/209,724, and PCT publication WO 2016/057811). Accordingly, Compound 1 is useful for treating one or more disorders associated with activity of GSNOR.

As used herein, the term "GSNOR inhibitor" or "S-nitrosoglutathione reductase inhibitor" means a compound which inhibits the enzyme S-nitrosoglutathione reductase and demonstrates activity in the enzyme assay described in the '181 application (e.g., GSNOR Assays as described in detail in Example 58 of the '181 application).

As used herein, the terms "treatment," "treat," and "treating" refer to reversing, alleviating, delaying the onset of, or inhibiting the progress of a disease or disorder, or one or more symptoms thereof, as described herein. In some embodiments, treatment may be administered after one or more symptoms have developed. In other embodiments, treatment may be administered in the absence of symptoms. For example, treatment may be administered to a susceptible individual prior to the onset of symptoms (e.g., in light of a history of symptoms and/or in light of genetic or other susceptibility factors). Treatment may also be continued after symptoms have resolved, for example to prevent or delay their recurrence.

Compound 1 is an inhibitor of GSNOR and is therefore useful for treating one or more disorders associated with the need for increased NO bioactivity. Thus, in certain embodiments, the present invention provides a method for treating a disorder characterized by decreased NO bioactivity comprising the step of administering to a patient in need thereof Compound 1, or pharmaceutically acceptable composition thereof.

Accordingly, another embodiment of the present invention relates to treating or lessening the severity of one or more diseases. Specifically, the present invention relates to a method of treating or lessening the severity of a disease or condition selected from pulmonary, inflammatory disorders, and vascular disorders wherein said method comprises administering to a patient in need thereof a compound or composition according to the present invention.

In some embodiments, the present invention provides a method for treating or lessening the severity of cystic fibrosis. In some embodiments, the present invention provides a method for treating or lessening the severity of COPD. In some embodiments, the present invention provides a method for treating or lessening the severity of asthma. In some embodiments, the present invention provides a method for treating or lessening the severity of IBD.

The present invention provides solid forms of Compound 1 that, as compared to Compound 1, may impart characteristics such as improved aqueous solubility, stability, and/or ease of formulation. In one embodiment, Compound 1 Form A may have improved stability. In other embodiments, Compound 1 Form A may have improved solubility. In another embodiment, Compound 1 Form A may offer improved ease of formulation.

Compound 1 and compositions thereof, according to the method of the present invention, may be administered using any amount and any route of administration effective for treating or lessening the severity of the disorder or disease. The exact amount required will vary from disease to disease, subject to subject, depending on the species, age, and general condition of the subject, the severity of the disease, the particular agent, its mode of administration, and the like. Compound 1 is preferably formulated in dosage unit form for ease of administration and uniformity of dosage. The expression "dosage unit form" as used herein refers to a physically discrete unit of agent appropriate for the patient to be treated. It will be understood, however, that the total daily usage of the compounds and compositions of the present invention will be decided by the attending physician within the scope of sound medical judgment. The specific effective dose level for any particular patient or organism will depend upon a variety of factors including the disorder being treated and the severity of the disorder; the activity of the specific compound employed; the specific composition employed; the age, body weight, general health, sex and diet of the patient; the time of administration, route of administration, and rate of excretion of the specific compound employed; the duration of the treatment; drugs used in combination or coincidental with the specific compound employed, and like factors well known in the medical arts.

Pharmaceutically acceptable compositions of this invention can be administered to humans and other animals orally, rectally, parenterally, intracisternally, intravaginally, intraperitoneally, topically (as by powders, ointments, or drops), bucally, as an oral or nasal spray, or the like, depending on the severity of the infection being treated. In certain embodiments, Compound 1 may be administered orally or parenterally at dosage levels of about 0.01 mg/kg to about 50 mg/kg and preferably from about 0.5 mg/kg to about 25 mg/kg, of subject body weight per day, one or more times a day, to obtain the desired therapeutic effect.

Liquid dosage forms for oral administration include, but are not limited to, pharmaceutically acceptable emulsions, microemulsions, solutions, suspensions, syrups and elixirs. In addition to Compound 1, the liquid dosage forms may contain inert diluents commonly used in the art such as, for example, water or other solvents, solubilizing agents and emulsifiers such as ethyl alcohol, isopropyl alcohol, ethyl carbonate, ethyl acetate, benzyl alcohol, benzyl benzoate, polyethylene glycol (e.g., PEG 200, PEG 400, PEG 1000, PEG 2000), propylene glycol, 1,3-butylene glycol, dimethylformamide, oils (in particular, cottonseed, groundnut, corn, germ, olive, castor, and sesame oils), glycerol, tetrahydrofurfuryl alcohol, Vitamin E polyethylene glycol succinate (d-alpha tocopheryl polyethylene glycol 1000 succinate), polyethylene glycols and fatty acid esters of sorbitan, and mixtures thereof. Besides inert diluents, the oral compositions can also include adjuvants such as wetting agents, emulsifying and suspending agents, sweetening, flavoring, and perfuming agents. The liquid forms above can also be filled into a soft or hard capsule to form a solid dosage form.

Suitable capsules can be formed from, for example, gelatin, starch and cellulose derivatives (e.g., hydroxycellulose, hydropropylmethylcellulose).

Injectable preparations, for example, sterile injectable aqueous or oleaginous suspensions may be formulated according to the known art using suitable dispersing or wetting agents and suspending agents. The sterile injectable preparation may also be a sterile injectable solution, suspension or emulsion in a nontoxic parenterally acceptable diluent or solvent, for example, as a solution in 1,3-butanediol. Among the acceptable vehicles and solvents that may be employed are water, Ringer's solution, U.S.P. and isotonic sodium chloride solution. In addition, sterile, fixed oils are conventionally employed as a solvent or suspending medium. For this purpose any bland fixed oil can be employed including synthetic mono- or diglycerides. In addition, fatty acids such as oleic acid are used in the preparation of injectables.

Injectable formulations can be sterilized, for example, by filtration through a bacterial-retaining filter, or by incorporating sterilizing agents in the form of sterile solid compositions which can be dissolved or dispersed in sterile water or other sterile injectable medium prior to use.

In order to prolong the effect of Compound 1 of the present invention, it is often desirable to slow the absorption of the compound from subcutaneous or intramuscular injection. This may be accomplished by the use of a liquid suspension of crystalline or amorphous material with poor water solubility. The rate of absorption of the compound then depends upon its rate of dissolution that, in turn, may depend upon crystal size and crystalline form. Alternatively, delayed absorption of a parenterally administered compound form is accomplished by dissolving or suspending the compound in an oil vehicle. Injectable depot forms are made by forming microencapsule matrices of the compound in biodegradable polymers such as polylactide-polyglycolide. Depending upon the ratio of compound to polymer and the nature of the particular polymer employed, the rate of compound release can be controlled. Examples of other biodegradable polymers include poly(orthoesters) and poly(anhydrides). Depot injectable formulations are also prepared by entrapping the compound in liposomes or microemulsions that are compatible with body tissues.

Compositions for rectal or vaginal administration are preferably suppositories which can be prepared by mixing Compound 1 of this invention with suitable non-irritating excipients or carriers such as cocoa butter, polyethylene glycol or a suppository wax which are solid at ambient temperature but liquid at body temperature and therefore melt in the rectum or vaginal cavity and release the active compound.

Solid dosage forms for oral administration include capsules, tablets, pills, powders, and granules. In such solid dosage forms, Compound 1 is mixed with at least one inert, pharmaceutically acceptable excipient or carrier such as sodium citrate or dicalcium phosphate and/or a) fillers or extenders such as starches, lactose, sucrose, glucose, mannitol, and silicic acid, b) binders such as, for example, carboxymethylcellulose, alginates, gelatin, polyvinylpyrrolidinone, sucrose, and acacia, c) humectants such as glycerol, d) disintegrating agents such as agar-agar, calcium carbonate, potato or tapioca starch, alginic acid, certain silicates, and sodium carbonate, e) solution retarding agents such as paraffin, f) absorption accelerators such as quaternary ammonium compounds, g) wetting agents such as, for example, cetyl alcohol and glycerol monostearate, h) absorbents such as kaolin and bentonite clay, and i) lubricants such as talc, calcium stearate, magnesium stearate, solid polyethylene glycols, sodium lauryl sulfate, and mixtures thereof. In the case of capsules, tablets and pills, the dosage form may also comprise buffering agents.

Solid compositions of a similar type may also be employed as fillers in soft and hard-filled capsules using such excipients as lactose or milk sugar as well as high molecular weight polyethylene glycols and the like. The solid dosage forms of tablets, dragees, capsules, pills, and granules can be prepared with coatings and shells such as enteric coatings and other coatings well known in the pharmaceutical formulating art. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes. Solid compositions of a similar type may also be employed as fillers in soft and hard-filled capsules using such excipients as lactose or milk sugar as well as high molecular weight polyethylene glycols and the like.

Compound 1 can also be in micro-encapsulated form with one or more excipients as noted above. The solid dosage forms of tablets, dragees, capsules, pills, and granules can be prepared with coatings and shells such as enteric coatings, release controlling coatings and other coatings well known in the pharmaceutical formulating art. In such solid dosage forms the active compound may be admixed with at least one inert diluent such as sucrose, lactose or starch. Such dosage forms may also comprise, as is normal practice, additional substances other than inert diluents, e.g., tableting lubricants and other tableting aids such a magnesium stearate and microcrystalline cellulose. In the case of capsules, tablets and pills, the dosage forms may also comprise buffering agents. They may optionally contain opacifying agents and can also be of a composition that they release the active ingredient(s) only, or preferentially, in a certain part of the intestinal tract, optionally, in a delayed manner. Examples of embedding compositions that can be used include polymeric substances and waxes.

Dosage forms for topical or transdermal administration of Compound 1 include ointments, pastes, creams, lotions, gels, powders, solutions, sprays, inhalants or patches. The active component is admixed under sterile conditions with a pharmaceutically acceptable carrier and any needed preservatives or buffers as may be required. Ophthalmic formulation, ear drops, and eye drops are also contemplated as being within the scope of this invention. Additionally, the present invention contemplates the use of transdermal patches, which have the added advantage of providing controlled delivery of a compound to the body. Such dosage forms can be made by dissolving or dispensing the compound in the proper medium. Absorption enhancers can also be used to increase the flux of the compound across the skin. The rate can be controlled by either providing a rate controlling membrane or by dispersing the compound in a polymer matrix or gel.

According to another embodiment, the invention relates to a method of inhibiting GSNOR activity in a biological sample comprising the step of contacting said biological sample with Compound 1, or a composition comprising the compound.

The term "biological sample", as used herein, includes, without limitation, cell cultures or extracts thereof; biopsied material obtained from a mammal or extracts thereof; and blood, saliva, urine, feces, semen, tears, or other body fluids or extracts thereof.

Another embodiment of the present invention relates to a method of inhibiting GSNOR activity in a patient comprising the step of administering to the patient Compound 1 or a composition comprising the compound.

In other embodiments, the present invention provides a method for treating a disorder mediated by one or more inhibitors of GNSOR in a patient in need thereof, comprising the step of administering to said patient Compound 1 or pharmaceutically acceptable composition thereof. Such disorders are described in detail herein.

Depending upon the particular condition, or disease, to be treated, additional therapeutic agents, which are normally administered to treat that condition, may also be present in the compositions of this invention or as part of a treatment regimen including Compound 1. As used herein, additional therapeutic agents that are normally administered to treat a particular disease, or condition, are known as "appropriate for the disease or condition being treated."

For example, Compound 1 or a pharmaceutically acceptable composition thereof is administered in combination with other CFTR modulators or anti-inflammatory agents.

The additional agents may be administered separately from a Compound 1-containing composition, as part of a multiple dosage regimen. Alternatively, those agents may be part of a single dosage form, mixed together with Compound 1 in a single composition. If administered as part of a multiple dosage regime, the two active agents may be submitted simultaneously, sequentially or within a period of time from one another (e.g., one hour, two hours, six hours, twelve hours, one day, one week, two weeks, one month).

As used herein, the terms "combination," "combined," and related terms refer to the simultaneous or sequential administration of therapeutic agents in accordance with this invention. For example, Compound 1 may be administered with another therapeutic agent simultaneously or sequentially in separate unit dosage forms or together in a single unit dosage form. Accordingly, the present invention provides a single unit dosage form comprising Compound 1, an additional therapeutic agent, and a pharmaceutically acceptable carrier, adjuvant, or vehicle.

The amount of Compound 1 and additional therapeutic agent (in those compositions which comprise an additional therapeutic agent as described above) that may be combined with the carrier materials to produce a single dosage form will vary depending upon the host treated and the particular mode of administration. Preferably, compositions of this invention should be formulated so that a dosage of between 0.01-100 mg/kg body weight/day of Compound 1 can be administered.

In those compositions that include an additional therapeutic agent, that additional therapeutic agent and Compound 1 may act synergistically. Therefore, the amount of additional therapeutic agent in such compositions may be less than that required in a monotherapy utilizing only that therapeutic agent. In such compositions, a dosage of between 0.01-1,000 rig/kg body weight/day of the additional therapeutic agent can be administered.

The amount of additional therapeutic agent present in the compositions of this invention will be no more than the amount that would normally be administered in a composition comprising that therapeutic agent as the only active agent. Preferably the amount of additional therapeutic agent in the presently disclosed compositions will range from about 50% to 100% of the amount normally present in a composition comprising that agent as the only therapeutically active agent.

All features of each of the aspects of the invention apply to all other aspects mutatis mutandis.

In order that the invention described herein may be more fully understood, the following examples are set forth. It should be understood that these examples are for illustrative purposes only and are not to be construed as limiting this invention in any manner.

EXEMPLIFICATION

As depicted in the Examples below, in certain exemplary embodiments, compounds are prepared according to the following general procedures. It will be appreciated that, although the general methods depict the synthesis of certain compounds of the present invention, the following general methods, and other methods known to one of ordinary skill in the art, can be applied to all compounds and subclasses and species of each of these compounds, as described herein.

Preparation of Compound 1

The synthesis of Compound 1 is described in detail at Example 8 of the '181 application, and included here below.

Synthesis of
3-chloro-4-(6-hydroxyquinolin-2-yl)benzoic Acid
(Compound 1)

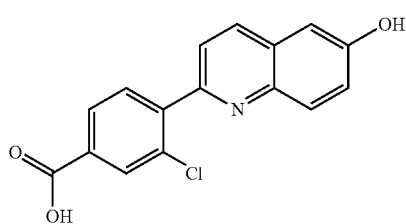

Step 1: Synthesis of
3-chloro-4-(6-methoxyquinolin-2-yl)benzoic Acid

A mixture of 2-chloro-6-methoxyquinoline (described in the '181 application as Intermediate 1) (200 mg, 1.04 mmol), 4-carboxy-2-chlorophenylboronic acid (247 mg, 1.24 mmol) and $K_2CO_3$ (369 mg, 2.70 mmol) in DEGME/$H_2O$ (7.0 mL/2.0 mL) was degassed three times under $N_2$ atmosphere. Then $PdCl_2(dppf)$ (75 mg, 0.104 mmol) was added and the mixture was heated to 110° C. for 3 hours under $N_2$ atmosphere. The reaction mixture was diluted with EtOAc (100 mL) and filtered. The filtrate was washed with brine (20 mL), dried over $Na_2SO_4$, filtered and concentrated to give 3-chloro-4-(6-methoxyquinolin-2-yl)benzoic acid (150 mg, yield 46%) as a yellow solid, which was used for the next step without further purification.

Step 2: Synthesis of
3-chloro-4-(6-hydroxyquinolin-2-yl)benzoic Acid

To a suspension of 3-chloro-4-(6-methoxyquinolin-2-yl)benzoic acid (150 mg, 0.479 mmol) in anhydrous $CH_2Cl_2$ (5 mL) was added $AlCl_3$ (320 mg, 2.40 mmol). The reaction mixture was refluxed overnight. The mixture was quenched with saturated $NH_4Cl$ (10 mL) and the aqueous layer was extracted with $CH_2Cl_2$/MeOH (v/v=10:1, 30 mL×3). The combined organic layer was washed with brine, dried over $Na_2SO_4$, filtered, and concentrated to give the crude product, which was purified by prep-HPLC (0.1% TFA as additive) to give 3-chloro-4-(6-hydroxyquinolin-2-yl)benzoic acid (25 mg, yield 18%). $^1$H NMR (DMSO, 400 MHz): δ 10.20 (brs, 1H), 8.30 (d, J=8.4 Hz, 1H), 8.10-8.00 (m, 2H), 7.95 (d, J=9.2 Hz, 1H), 7.80 (d, J=8.0 Hz, 1H), 7.72 (d, J=8.8 Hz, 1H), 7.38 (dd, J=6.4, 2.8 Hz, 1H), 7.22 (d, J=2.4 Hz, 1H), MS (ESI): m/z 299.9 [M+H]$^+$.

General Procedures

X-ray powder diffraction data were collected in transmission mode with a PAN analytical X'Pert PRO MPD diffractometer using an incident beam of Cu radiation (1.54059 Å) produced using an Optix long, fine-focus source. An elliptically graded multilayer mirror was used to focus Cu Kα X-rays through the specimen and onto the detector. Prior to the analysis, a silicon specimen (NIST SRM 640d) was analyzed to verify the observed position of the Si 111 peak is consistent with the NIST-certified position. A specimen of the sample was sandwiched between 3-jam-thick films and analyzed in transmission geometry. A beam-stop, short anti-scatter extension, anti-scatter knife edge, were used to minimize the background generated by air. Soller slits for the incident and diffracted beams were used to minimize broadening from axial divergence. Diffraction patterns were collected using a scanning position-sensitive detector (X'Celerator) located 240 mm from the specimen and Data Collector software v. 2.2b. A scan range of 1.00°2θ to 39.99°2θ with a step size of 0.017°2θ was used to collect data over a range of 716 to 721 seconds with a scan speed of 3.2 to 3.3°/minute and a revolution time of 1.0 second. A divergence slit was set at ½° before the mirror.

Thermogravimetric data were collected using a TA Instruments 2050 thermogravimetric analyzer. Temperature calibration was performed using nickel and Alumel™. Each sample was placed in a platinum pan and inserted into the TG furnace. The furnace was heated under a nitrogen purge. The sample was heated from ambient to 350° C. at 10° C./minute.

Differential scanning calorimetric analysis: data were collected using a TA Instruments Q2000 differential scanning calorimeter. Temperature calibration was performed using NIST-traceable indium metal. The sample was placed into a T zero aluminium DSC pan, covered with a lid and crimped. The weight was then accurately recorded. A weighed aluminum pan configured as the sample pan was placed on the reference side of the cell. The sample was heated from −30° C. to 300° C. at 10° C./minute.

Solution proton nuclear magnetic resonance analysis for Compound 1 Form A was acquired at ambient temperature with an Agilent DD2-400 spectrometer at a $^1$H Larmor frequency of 399.822 MHz. The sample was dissolved in deuterated dimethylsulfoxide containing tetramethylsilane. The spectrum was acquired with a $^1$H pulse width of 6.8 µs, a 5 second acquisition time, a 2.5 second delay between scans, a spectral width of 6410.3 Hz with 64102 data points, and 40 co-added scans. The free induction decay was processed using Varian VNMR 6.1C software with 131072 points and an exponential line broadening factor of 0.2 Hz to improve the signal-to-noise ratio.

Solution proton nuclear magnetic resonance analyses for Compound 1 Form B, Form C and Form D were acquired on a Varian UNITYINOVA-400 spectrometer at a $^1$H Larmor frequency of 399.667 MHz. The samples were dissolved in deuterated dimethylsulfoxide containing tetramethylsilane. The $^1$H NMR spectrum represents 40 co-added transients collected with a 6 msec pulse and a relaxation delay time of 5 seconds. The free induction decay (FID) was exponentially multiplied with a 0.2 Hz Lorentzian line broadening factor to improve the signal-to-noise ratio.

For Karl Fischer (KF) Coulometric titration, 40 to 60 mg of solid material was accurately weighed into a weighting paper. The solid was then manually introduced into the titration cell of a Metrohm 756 KF Coulometer. Titration was initiated once the sample had fully dissolved in the cell. The water content was calculated automatically by the instrument as a percentage and the data printed.

Reverse-phase gradient high performance liquid chromatography (HPLC) was performed on an Agilent 1100/1200 instrument fitted with a C18, 4.6×100 mm Atlantis T3 column. The detection wavelength was 268 nm.

Example 1: Form A

Example Preparation of Form A

Compound 1 (66.72 mg) was stirred at approximately 60° C. in ethanol/water (13/9 v/v) (400 μl). After stirring overnight, solids were isolated by centrifugation using a Spin-X centrifuge tube equipped with a 0.45 μm nylon filter, and vacuum dried at approximately 65° C. overnight. A portion of the solids (37.1 mg) was stirred at approximately 60° C. in ethanol/water (13/9 v/v) (400 μl) for 2 weeks, after which the solids were isolated by centrifugation as described above, and analyzed by X-ray powder diffraction as a wet residue. XRPD result indicated the solids were composed of Form A.

Characterization of Form A

Figure 2:
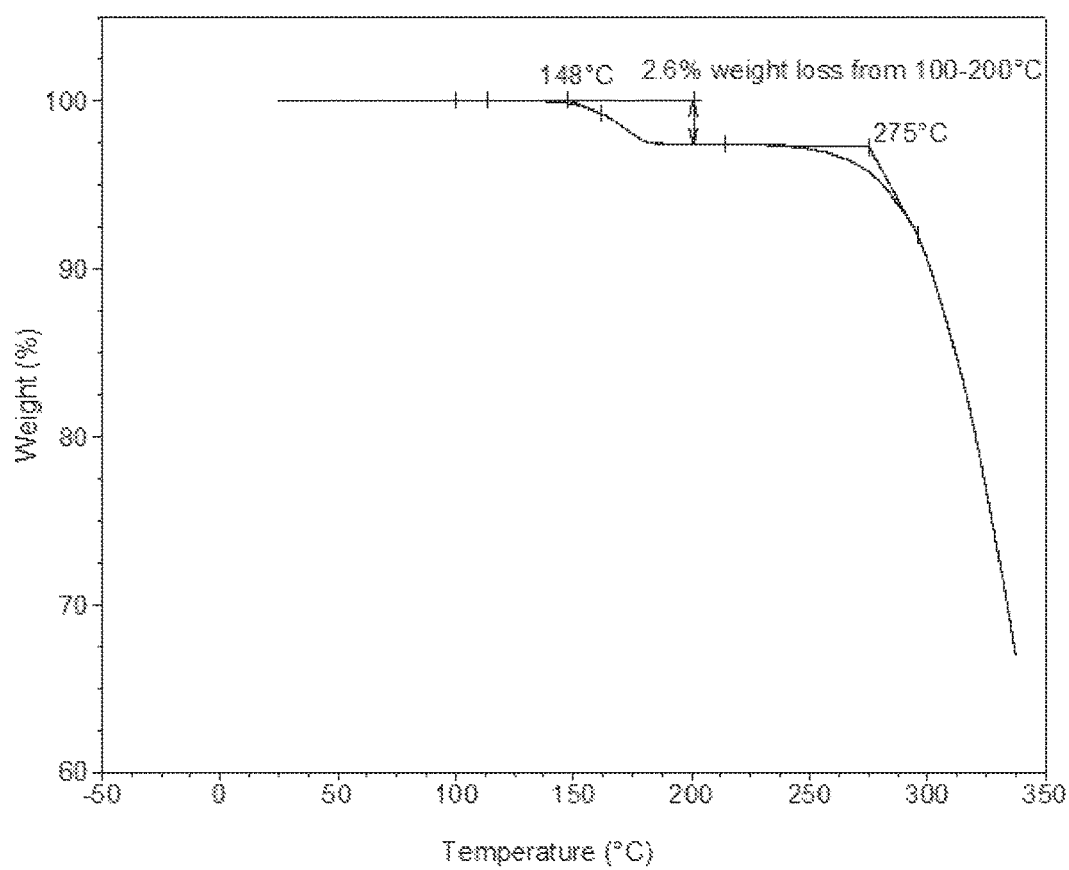
FIG. 2 depicts the thermogravimetric thermogram (TGA) of Form A of Compound 1.
Figure 3:
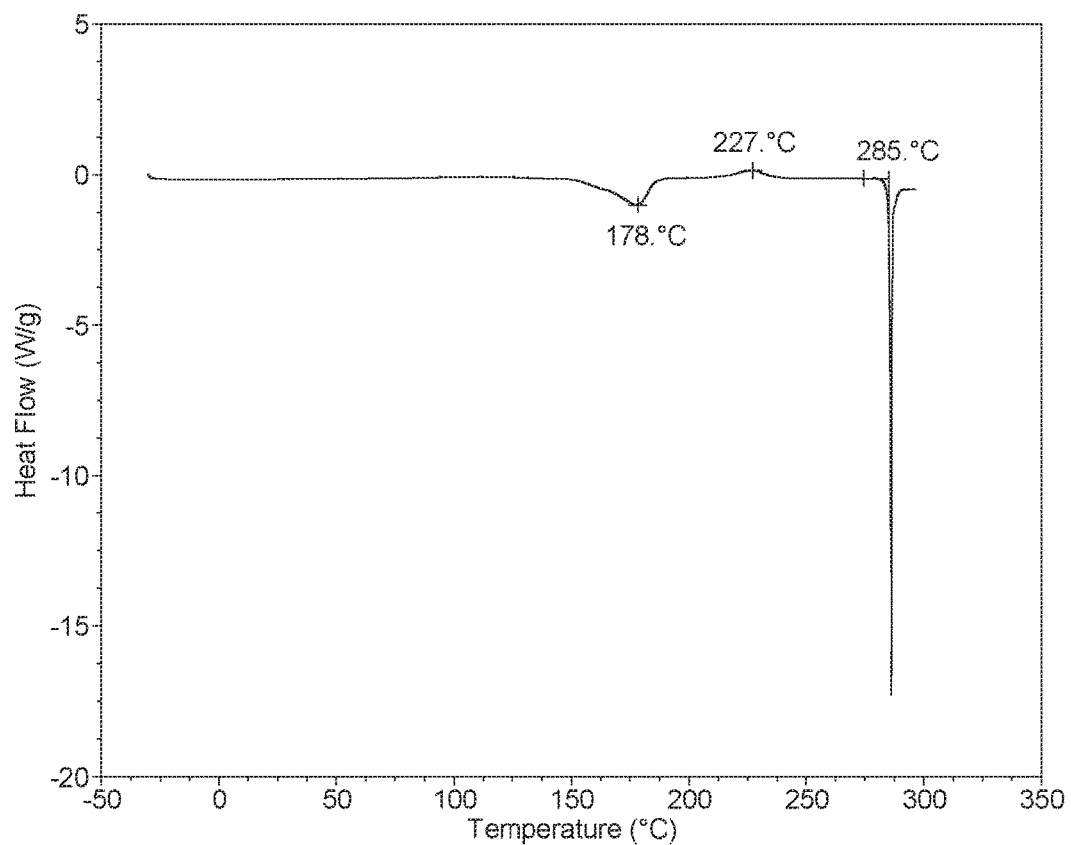
FIG. 3 depicts the differential scanning calorimetry (DSC) pattern for Form A of Compound 1.
Figure 4:
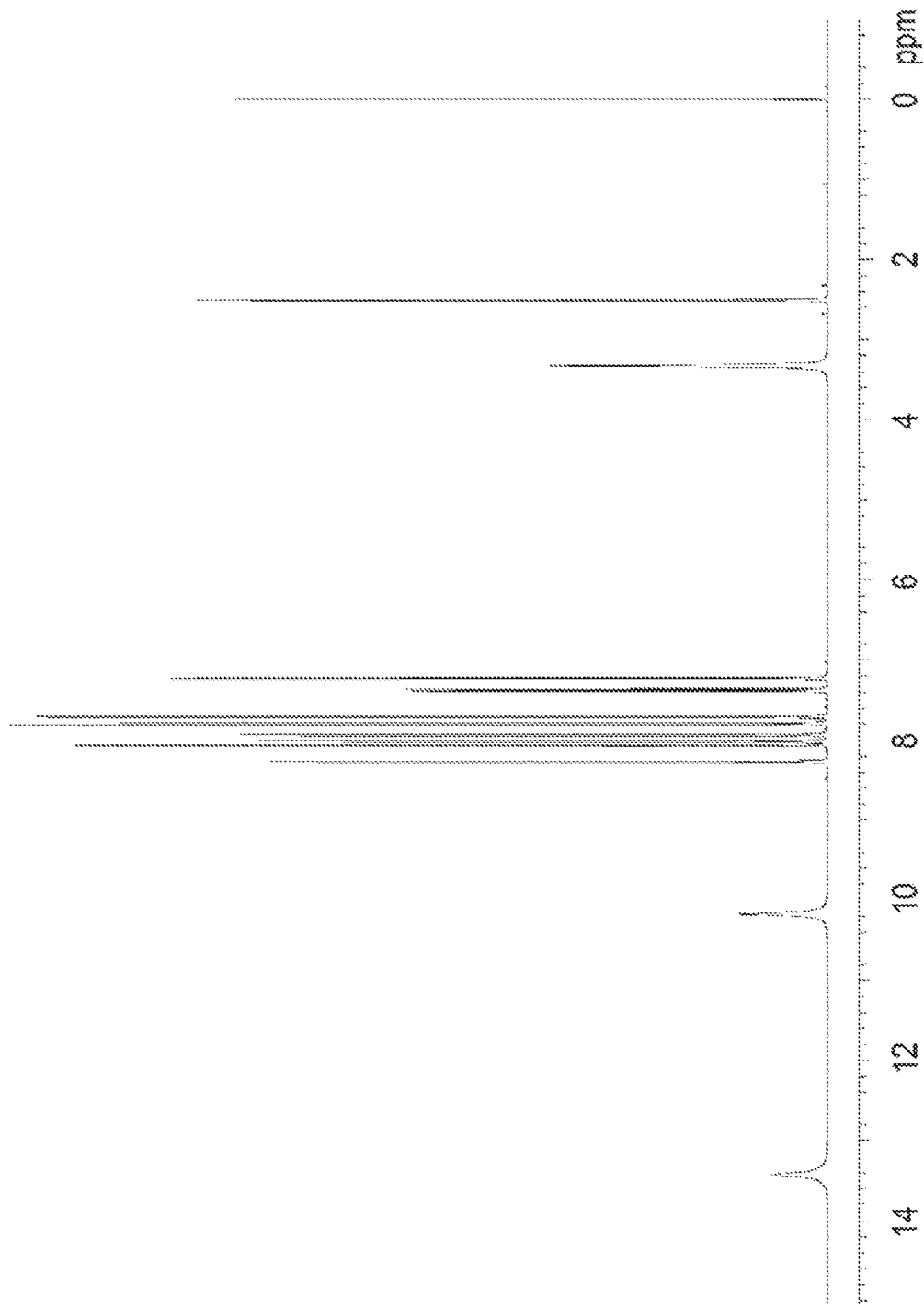
FIG. 4 depicts the $^1$H NMR spectrum for Form A of Compound 1.

XRPD analysis showed Form A to be crystalline (see FIG. 1). By TGA, a step-like weight loss of approximately 2.6% is seen with an onset at approximately 148° C., and is followed by a sharp weight loss at onset ~275° C. likely associated with decomposition (FIG. 2). DSC for Form A shows an endotherm at approximately 178° C. (peak), which is likely associated with the water loss. On further heating, an exothermic event at approximately 227° C. and an endotherm at about 285° C. (onset) are observed, which likely indicate a form transition and melting of the new form (FIG. 3). $^1$H NMR (FIG. 4) carried out in deuterated DMSO showed a spectrum consistent with the structure of Compound 1. KF analysis (not shown) analysis indicated the presence of ca. 2.93% water, consistent with the hemi-hydrate.

Example 2: Form B

Example Preparation of Form B

Compound 1 (66.17 mg) was stirred at ambient temperature in ethanol/water (96.9/3.1 v/v) (200 μl). After stirring overnight, solids were isolated by centrifugation using a Spin-X centrifuge tube equipped with a 0.45 μm nylon filter, and vacuum dried at approximately 65° C. overnight. A portion of the solids (54.6 mg) was stirred at ambient temperature in ethanol/water (96.9/3.1 v/v) (300 μl) for 2 weeks, after which the solids were isolated by centrifugation as described above and analyzed by X-ray powder diffraction as a wet residue.

Characterization of Form B

XRPD analysis (FIG. 5) showed Form B to be crystalline. TGA (FIG. 6) analysis of Form B showed negligible weight loss from ambient to 200° C. and the onset of decomposition occurring at approximately 281° C. DSC (FIG. 7) showed an endotherm at onset 282.0 (peak 284.29). $^1$H NMR (FIG. 8) carried out in deuterated DMSO showed a spectrum which corresponded with the free form. KF (not shown) analysis indicated the presence of ca. 0.5% water.

Example 3: Form C

Example Preparation of Form C

Compound 1 (55.31 mg) was stirred at ambient temperature in isopropyl alcohol (IPA)/toluene (4:1 v/v, 200 μl). After stirring overnight, solids were isolated by centrifugation using a Spin-X centrifuge tube equipped with a 0.45 μm nylon filter, and vacuum dried at approximately 65° C. overnight. A portion of the solids (45.3 mg) was stirred at ambient temperature in IPA/toluene (4:1 v/v, 250 μl) for 2 weeks, after which the solids were isolated by centrifugation as described above and air dried. X-ray powder diffraction indicated the solids were composed of Form C.

Characterization of Form C

XRPD analysis (FIG. 9) showed Form C to be crystalline. TGA (FIG. 10) of Form C shows negligible weight loss from ambient to 100° C. and a step-like weight loss of about 8.7% from 100 to 200° C. The onset of decomposition was observed at approximately 279° C. $^1$H NMR (FIG. 11) analysis carried out in deuterated DMSO indicates presence of 0.5 mol of IPA per mol of Compound 1.

Example 4: Form D

Example Preparation of Form D

Compound 1 (19.91 mg) was dissolved at approximately 65° C. in ethanol/water (13/9 v/v) (2.2 ml). The solution was filtered warm through a 0.45 μm polytetrafluoroethylene (PTFE) filter into a vial that was maintained in an ice bath. Crystallization was observed while sample was in ice bath. Sample was removed from ice bath and left at ambient for approximately 1 hour, additional crystallization was observed. The solids were isolated by centrifugation using a Spin-X centrifuge tube equipped with a 0.45 μm nylon filter and analyzed. X-ray powder diffraction indicated the solids were composed of Form D.

Characterization of Form D

XRPD analysis (FIG. 12) showed Form D to be crystalline. TGA (FIG. 13) shows a weight loss of ~8.8% from ambient to 150° C. which is likely due to loss of water and ethanol. The onset of apparent decomposition occurred at 273° C. $^1$H-NMR (FIG. 14) carried out in deuterated DMSO showed a spectrum which corresponds with 0.02 mol of ethanol per mol of Compound 1. Based on TGA and 1HNMR, form D could be a hydrate of Compound 1.

I claim:
1. A crystalline solid form of Compound 1,

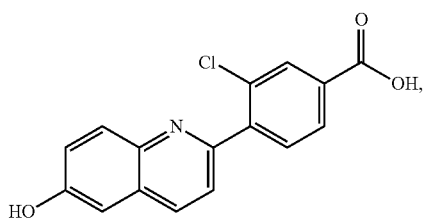 [SMILES: O=C(O)c1ccc(-c2ccc3cc(O)ccc3n2)c(Cl)c1]

wherein Compound 1 is a free form.
2. The crystalline solid form of claim 1, wherein the solid form is a hemi-hydrate.

3. The crystalline solid form of claim 2, wherein the solid form is Form A.

4. The crystalline solid form of claim 3 wherein Form A of Compound 1 is characterized by peaks in its powder X-ray diffraction pattern at about 12.9 and one or more additional peaks selected from those at about 18.0, about 18.9, about 22.6, about 23.0, about 23.7, and about 24.9 degrees 2-theta.

5. The crystalline solid form of claim 1, wherein Compound 1 is unsolvated.

6. The crystalline solid form of claim 5, wherein the solid form is Form B.

7. The crystalline solid form of claim 6 wherein Form B of Compound 1 is characterized by a peaks in its powder X-ray diffraction pattern at about 21.4 and one or more additional peaks selected from those at about 14.3, about 18.0, about 18.7, about 22.3, about 25.7, and about 27.6 degrees 2-theta.

8. The crystalline solid form of claim 1, wherein Compound 1 is an IPA solvate.

9. The crystalline solid form of claim 8, wherein the solid form is Form C.

10. The crystalline solid form of claim 9, wherein Form C of Compound 1 is characterized by peaks in its powder X-ray diffraction pattern at about 19.4 and one or more additional peaks selected from those at about 8.1, about 11.4, about 17.7, about 18.9, about 20.5, and about 25.2 degrees 2-theta.

11. The crystalline solid form of claim 1, wherein the solid form is form D.

12. The crystalline solid form of claim 11, wherein Form D of Compound 1 is characterized by a peaks in its powder X-ray diffraction pattern at about 5.5 and one or more additional peaks selected from those at about 9.4, about 22.5, about 23.8, about 25.0, about 27.2, and about 27.3 degrees 2-theta.

13. A composition comprising the crystalline solid form of claim 1 and a pharmaceutically acceptable carrier or excipient.

14. A method for inhibiting S-nitrosoglutathione reductase, in a biological sample or in a patient, comprising contacting the biological sample with, or administering to the patient, a crystalline solid form according to claim 1, or a composition thereof.

15. A method for treating a disorder or condition in a patient, comprising administering to the patient a composition according to claim 13.

16. The method of claim 15, wherein the disorder or condition is selected from the group consisting of cystic fibrosis, asthma, COPD, and IBD.

* * * * *